(12) United States Patent
Hodson et al.

(10) Patent No.: US 7,407,954 B2
(45) Date of Patent: Aug. 5, 2008

(54) THIENO-(1,3)-OXAZIN-4-ONES WITH LIPASE INHIBITING ACTIVITY

(75) Inventors: Harold Francis Hodson, Beckenham (GB); Christopher Robert Dunk, Ely (GB); Richard Michael John Palmer, Beckenham (GB); Dale Robert Mitchell, Great Chesterford (GB); Véronique Birault, Widdington (GB); Russell George Hunt, Harston (GB)

(73) Assignee: Alizyme Therapeutics Limited, Great Abington (GB)

( * ) Notice: Subject to any disclaimer, the term of this patent is extended or adjusted under 35 U.S.C. 154(b) by 223 days.

(21) Appl. No.: 10/488,045

(22) PCT Filed: Aug. 23, 2002

(86) PCT No.: PCT/GB02/03903

§ 371 (c)(1),
(2), (4) Date: Nov. 1, 2004

(87) PCT Pub. No.: WO03/020282

PCT Pub. Date: Mar. 13, 2003

(65) Prior Publication Data

US 2005/0075336 A1    Apr. 7, 2005

(30) Foreign Application Priority Data

Aug. 30, 2001 (GB) ................. 0121019.4
Mar. 14, 2002 (GB) ................. 0206031.7

(51) Int. Cl.
C07D 498/04 (2006.01)
A61K 31/538 (2006.01)

(52) U.S. Cl. .................... 514/230.5; 544/91
(58) Field of Classification Search ............. 544/91; 514/230.5
See application file for complete search history.

(56) References Cited

U.S. PATENT DOCUMENTS 4,598,089 A   7/1986   Hadvary et al. ............. 514/449
4,760,063 A   7/1988   Hallenbach et al. ...... 514/230.5

FOREIGN PATENT DOCUMENTS

| EP | 0 129 748 | 1/1985 |
|---|---|---|
| EP | 0 908 457 | 4/1999 |
| EP | 0 985 670 | 3/2000 |
| JP | 2002-105081 | 4/2002 |
| WO | WO 00/30646 | 6/2000 |
| WO | WO 00/40247 | 7/2000 |
| WO | WO 00/40569 | 7/2000 |
| WO | WO 01/18181 | 3/2001 |
| WO | WO 01/53278 | 7/2001 |
| WO | WO 03/053944 | 7/2003 |

OTHER PUBLICATIONS

Chalmers (TiPS vol. 17, pp. 166-172 Apr. 1996).*
Thomas A. Godwin (Gastrointestinal Diseases, <http://edcenter.med.cornell.edu/CUMC_PathNotes/Gastrointestinal/Gastrointestinal.html>, 51 pages) downloaded on Aug. 11, 2004.*
Gutschow et al. J. Med. Chem. 1998, 41, 1729-1740.*
Wolff Manfred E. "Burger's Medicinal Chemistry, 5ed, Part 1", John Wiley & Sons, 1995, pp. 975-977.*
Banker, G.So et al, "Modern Pharmaceutices, 3ed.", Marcel Dekker, New York. 1996, pp. 451 and 596.*
Hu, Aixi, "Application Of Bioisosteric Principle In Drug Molecular Design.", *Hunan Chemical Industry*2(4): 7-10, 1990. (Original in Chinese/ English Translation Enclosed).
Garin, et al., "Methyl N-Aryldithiocarbamates: Useful Reagents for the Annelation of Pyrimidines and 1,3-Oxazines to Five-Membered Heterocyclic Rings", *Heterocycles*, 26(5): 1303-1312, 1987.
Gütschow, et al., "2-(Diethylamino) Thieno[1,3]Oxazin-4-Ones as Stable Inhibitors of Human Leukocyte Elastase", *J. Med. Chem.* 42: 5437-5447, 1999.
Gütschow, et al., "Novel Thieno [2,3-d][1,3] Oxazin-4-Ones as Inhibitors of Human Leukocyte Elastase", *J. Med. Chem.* 41: 1729-1740, 1998.
Krantz, et al., "Design and Synthesis of 4H-3,1-Benzoxazin-4-Ones as Potent Alternate Substrate Inhibitors of Human Leukocyte Elastase", *J. Med. Chem.* 33: 464-479, 1990.

(Continued)

*Primary Examiner*—Kahsay T Habte
(74) *Attorney, Agent, or Firm*—Choate Hall & Stewart LLP

(57) ABSTRACT

The use of a compound comprising formula (I), or a salt, ester, amide or prodrug thereof in the treatment of obesity and related disorders. The invention also relates to novel compounds within formula (I), to processes for preparing them and pharmaceutical compositions containing them. In formula (I): A is an optionally substituted thienyl moiety, Y is O, S, or $NR^2$, $R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups and $R^2$ is hydrogen or a group as defined for $R^1$.

(I)

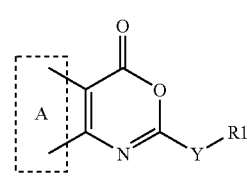

29 Claims, No Drawings

OTHER PUBLICATIONS

Pasquier, et al., "Viscous Soluble Dietary Fibers Alter Emulsification and Lipolysis of Triacylglycerols in Duodenal Medium in Vitro", *J. Nutr. Biochem.* 7: 293-302, 1996.

Pietsch, et al., "Alternate Substrate Inhibition of Cholesterol Esterase by Thieno[2,3-d][1,3]Oxazin-4-Ones", *The Journal of Biological Chemistry*, 277(27): 24006-24013, 2002.

Player, et al., "Preparation of Fused 1,3-Oxazine-2,4-Diones as Potential Antitumor Agents", *J. Heterocyclic Chem.* 32: 1537-1540, 1995.

Wang, et al., "A New Approach to the Synthesis of Heteroannulated 3,1-Oxazin-4-Ones from β-Enamino Esters and Phosgeneiminium Salts", *Synthesis*, 2: 255-258, 2000.

\* cited by examiner

THIENO-(1,3)-OXAZIN-4-ONES WITH LIPASE INHIBITING ACTIVITY

This application is a U.S. national phase application under 35 U.S.C. § 371 of international application No. PCT/GB02/03903 filed Aug. 23, 2002, which international application claims priority to GB 0121019.4 filed Aug. 30, 2001 and GB 0206031.7 filed Mar. 14, 2002. International application No. PCT/GB02/03903 was filed in English and designated the United States. The entire contents of each of these applications is hereby incorporated by reference.

The present invention provides thieno-oxazinone compounds, their use in medicine, and particularly in the prevention and/or treatment of obesity or an obesity-related disorder, such as diabetes, and their use in the inhibition of an enzyme whose preferred mode of action is to catalyse the hydrolysis of an ester functionality. Also provided are methods for the prevention and/or treatment of obesity or an obesity-related disorder and for promoting/aiding non-medical weight loss and the use of the compounds in the manufacture of a medicament for the aforementioned indications. The invention also provides processes for manufacture of said compounds, compositions containing them and methods for manufacturing such compositions.

In the last 20 years, there has been an increasing trend in obesity in the populations of the developed world. The increased incidence of obesity is due in part to the ready availability of food in numerous retail outlets and westernised diets that have high saturated fat and lower fibre contents such that the food is energy dense. The lifestyle of the populations of the developed world has also become more sedentary with the increased mechanisation of society and the steady reduction of manual labour intensive industries. There now exists an energy imbalance between the energy intake from calorie dense foods and the reduced energy expenditure required for a sedentary lifestyle. Some of the excess energy intake is stored as fat in the adipose tissue, the accumulation of which over a period of time results in obesity and can be a significant contributory factor to other disease and disorders.

Obesity is now recognised by the medical profession as a metabolic disease. In the USA, it is estimated that 25% of the adult population is considered clinically obese (Body Mass Index>30). Obesity can be a debilitating condition which reduces the quality of life and increases the risk of related disorders such as diabetes, cardiovascular disease and hypertension. It has been estimated that $45 billion of US healthcare costs, or 8% per annum of total healthcare spend, is as a direct result of obesity. The traditional approaches to long term weight management such as diet and exercise have proved ineffective alone to control the spread of obesity. Today, more than ever, there is considerable interest in developing safe, effective drugs for the treatment of obesity.

Pharmacological approaches to the treatment of obesity have focused on either developing drugs that increase energy expenditure or drugs that reduce energy intake.

One approach to the reduction of energy intake is to reduce the body's ability to digest and absorb food, in particular fat. The key enzymes involved in the digestion of fat are hydrolytic enzymes. The most significant of the fat degrading enzymes are lipases, primarily, but not exclusively pancreatic lipase that is secreted by the pancreas into the gut lumen. The lipase inhibitor tetrahydrolipstatin has formed the basis of the anti-obesity drug, orlistat. European Patent Application No. EP129748 relates to orlistat and related compounds and their use in inhibiting pancreatic lipase and treating hyperlipaemia and obesity.

Even if orlistat provides an effective method for treating obesity, there remains a need to provide alternative drugs and methods for use in the control and treatment of obesity and obesity-related disorders and in promoting or aiding non-medical weight loss. Inhibitors of enzymes involved in the degradation of fat are provided here and shown to be effective in the prevention and/or treatment of obesity, obesity-related disease and/or in promoting cosmetic weight loss.

U.S. Pat. No. 4,760,063 (Hallenbach et al) discloses the synthesis of 2-amino-thieno-oxazines of the formula or

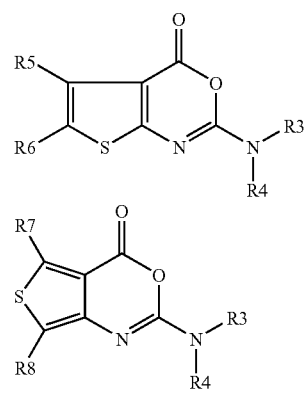

The use of these compounds as growth promoters for non-human animals is discussed.

Player et al (J. Heterocyclic Chem., 32, 1537-1540, (1995) discusses six oxazinone compounds. These compounds are based on a series of substituted indole-, thiophene- and pyrrole-fused 2-dimethylamino-1,3-oxazin-4-one. This paper relates to the preparation of these compounds and their evaluation as anti-tumour agents.

EP-A-0985670 and EP-A-0908457 (American Cyanamid Company) discloses the synthesis of 1-(3-heterocyclylphenyl)isothiourea, isourea, guanidine and amidine compounds and their use as herbicides.

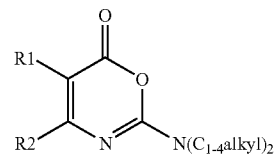

The synthesis of these compounds involves the oxazinone intermediate illustrated above where $R^1$ and $R^2$ can be a 4 to 7 membered ring optionally interrupted with nitrogen, sulphur or oxygen and substituted with 1 to 3 methyl groups or one or more halogen atoms.

International application numbers PCT/GB00/00031, PCT/GB00/00032, and PCT/GB01/00171 relate to 2-amino, 2-oxy and 2-thio-benzoxazinone compounds. These applications relate to the use of these compounds in the control and treatment of obesity and obesity related disorders.

We have now found that a particular class of thieno-oxazinone compounds has activity as lipase inhibitors.

Accordingly, in a first aspect, the present invention provides the use of a compound of formula (I):

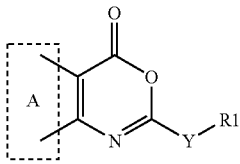
(I)

or a pharmaceutical acceptable salt, ester, amide or prodrug thereof; in the manufacture of a medicament for the prevention or treatment of obesity or an obesity related disorder; wherein in formula (I): A is an optionally substituted thienyl moiety, Y is O, S, or $NR^2$, and $R^1$ is a branched or unbranched alkyl (optionally interrupted by one or more oxygen atoms), alkenyl, alkynyl, cycloalkyl, cycloalkenyl, aryl, arylalkyl, reduced arylalkyl, arylalkenyl, heteroaryl, heteroarylalkyl, heteroarylalkenyl, reduced aryl, reduced heteroaryl, reduced heteroarylalkyl or a substituted derivative of any of the foregoing groups, wherein the substituents are one or more independently of halogen, alkyl, halosubstituted alkyl, aryl, arylalkyl, heteroaryl, reduced heteroaryl, reduced heteroarylalkyl, arylalkoxy, cyano, nitro, —$C(O)R^4$, —$CO_2R^5$, —$SOR^4$, —$SO_2R^4$, —$NR^6R^7$, —$OR^6$, —$SR^6$, —$C(O)CX^1X^2NR^6R^7$, —$C(O)N(OR^5)R^6$, —$C(O)NR^5R^4$, —$NR^6C(O)R^4$, —$CR^6(NH_2)CO_2R^6$, —$NHCX^1X^2CO_2R^6$, —$N(OH)C(O)NR^6R^7$, —$N(OH)C(O)R^4$, —$NHC(O)NR^6R^7$, —$C(O)NHNR^6R^7$, —$C(O)N(OR^5)R^6$, or a lipid or steroid (natural or synthetic) with the proviso that any hetero atom substituent in $R^1$ must be separated from the exocyclic hetero-atom by at least two carbon atoms (preferably saturated);

and where:

$R^2$ is hydrogen or a group as defined above for $R^1$ $R^4$ is hydrogen, alkyl, alkenyl, alkynyl, cycloalkyl, cycloalkenyl, aryl, arylalkyl, heteroaryl, heteroarylalkyl, reduced heteroaryl, reduced heteroarylalkyl, —$OR^6$, —$NHCX^1X^2CO_2R^6$ or —$NR^6R^7$ or a substituted derivative of any of the foregoing groups;

$R^5$ is hydrogen, alkyl, alkenyl, alkynyl, cycloalkyl, cycloalkenyl, aryl, arylalkyl heteroaryl, heteroarylalkyl, reduced heteroaryl or reduced heteroarylalkyl; and $R^6$ and $R^7$ are independently hydrogen, alkyl, alkenyl, alkynyl, cycloalkyl, cycloalkenyl, aryl, arylalkyl, heteroaryl, reduced heteroaryl, reduced heteroarylalkyl or —$(CH_2)n(OR^5)m$ wherein n is 1 to 12, preferably 2 to 10, wherein m is 1-3 or a substituted derivative of any of the foregoing groups;

and $R^5$ is most preferably $C_2$-$C_{10}$ alkyl; and $X^1$ and $X^2$ are independently hydrogen, alkyl, alkenyl, alkynyl, cycloalkyl, cycloalkenyl, aryl, heteroaryl, arylalkyl, heteroarylalkyl, reduced heteroaryl or reduced heteroarylalkyl wherein for the groups $R^1$, $R^2$, $R^4$, $R^5$, $R^6$, $R^7$, $X^1$ and $X^2$, preferably the alkyl groups have from 1 to 30 carbon atoms, the alkenyl groups have 2 to 30 carbon atoms, the alkynyl groups have 2 to 30 carbon atoms, the cycloalkyl groups have 3 to 30 carbon atoms, the cycloalkenyl groups have 3 to 30 carbon atoms, the aryl groups have 6 to 12 carbon atoms and the heteroaryl groups have 5 to 12 atoms.

The thienyl moiety is fused to the oxazinone ring in the 2,3-position, 3,4-postion or the 3,2-position as illustrated below;

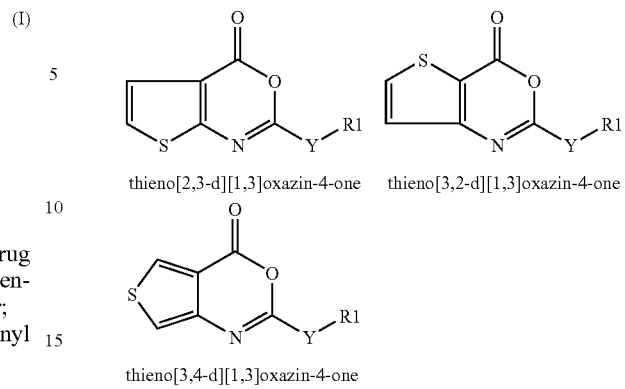

thieno[2,3-d][1,3]oxazin-4-one    thieno[3,2-d][1,3]oxazin-4-one thieno[3,4-d][1,3]oxazin-4-one Preferably the thienyl moiety is fused to the oxazinone ring in the 2,3-position or the 3,2-position.

The thienyl moiety A may optionally be substituted with one or more of hydrogen, hydroxy, halogen, oxo, amino, nitro, cyano, alkyl, aryl, alkylaryl, haloalkyl, alkoxy, aryloxy, alkylthio, alkylamino, arylthio or arylamino wherein arylthio, arylamino and aryloxy can be substituted by one or more of halo, alkyl, haloalkyl, alkoxy, thioalkyl, or aminoalkyl; the thienyl moiety A may be optionally substituted by a group $R^{12}Q$ where Q is O, CO, CONH, NHCO, S, SO, $SO_2$, or $SO_2NH_2$ and $R^{12}$ is hydrogen or a group $R^1$ as defined above; or a group $R^1R^{14}N$ where $R^1$ is as defined above and $R^{14}$ is H or $R^1$, with the proviso that any hetero atom substituent in $R^1$ and/or $R^{14}$ must be separated from the aromatic hetero atom substituent by at least two carbon atoms (preferably saturated);

wherein for the substituents for the thienyl moiety A, preferably the alkyl groups have from 1 to 30 carbon atoms, the alkenyl groups have 2 to 30 carbon atoms, the alkynyl groups have 2 to 30 carbon atoms, the cycloalkyl groups have 3 to 30 carbon atoms, the cycloalkenyl groups have 3 to 30 carbon atoms, the aryl groups have 6 to 12 carbon atoms and the heteroaryl groups have 5 to 12 atoms.

In addition, the thienyl group can be further fused to one or more five, six or seven membered aryl, heterocyclic, or cycloalkyl rings. Examples of heterocyclic groups containing such fused rings include benzothiophene. The fused ring may optionally be saturated.

Preferably, the thienyl group A is optionally substituted with one or more of alkyl, aryl, halo, alkoxy, haloalkyl, aryloxy, amino, heteroaryl, or arylalkyl. More preferably the thienyl moiety A is optionally substituted with one or more of hydrogen, branched or unbranched alkyl having 1 to 20 carbon atoms, cyclic alkyl having 3 to 10 carbon atoms, aryl, haloalkyl, or a halogen;

Y is preferably O, S or $NR_2$;

$R^1$ is preferably alkyl, or aryl, optionally substituted with alkyl, haloalkyl, halo, cyano, nitro, $OR^6$, $SR^6$, $COR^6$, $CO_2R^6$, $NR^6$, $R^7$, or aryl optionally substituted with aryloxy, arylthio, SO-aryl, $SO_2$-aryl alkylaryl, CO-aryl, $CO_2$-aryl, $CONR^6$-aryl, $NR^6CO$-aryl or $NR^6$-aryl or a substituted derivative of any of the foregoing groups.

$R^2$ is preferably hydrogen or alkyl.

With respect to the groups $R^1$, $R^2$, $R^4$, $R^5$, $R^6$, $R^{12}$, $X^1$ and $X^2$, any alkyl, alkenyl and alkynyl groups and moieties may be straight chain (unbranched) or branched chain. Straight chain alkyl, alkenyl and alkynyl groups or moieties may contain from 1 to 30 carbon atoms, eg. 1 to 25 carbon atoms, preferably 1 to 20 carbon atoms. Branched chain alkyl, alkenyl and alkynyl groups or moieties may contain from 1 to 50 carbon atoms, preferably 1 to 30 carbon atoms.

Preferably, where $R^1$ is an alkyl group, the alkyl group preferably has from 4 to 30 carbon atoms, more preferably from 4 to 20 carbon atoms. In particular, $R^1$ is an unbranched alkyl with 8, 9, 10, 11, 12, 13, 14, 15, 16, 17, 18, 19 or 20 carbon atoms.

Where one or more of $R^2$, $R^4$, $R^5$, $R^6$, $R^{12}$, $X^1$ and $X^2$ is an alkyl group, the alkyl group can be a straight (unbranched) or branched chain. Straight or branched chain alkyl groups or moieties may contain from 1 to 10 carbon atoms, e.g. 1 to 8 carbon atoms, preferably 1 to 5 carbon atoms. Examples of such alkyl groups include methyl, ethyl, n-propyl, isopropyl, n-butyl, isobutyl, sec-butyl, t-butyl, n-pentyl.

Aryl groups include for example optionally substituted unsaturated monocyclic or bicyclic rings of up to 12 carbon atoms, such as phenyl and naphthyl, and partially saturated bicyclic rings such as tetrahydro-naphthyl. Preferably, the aryl group is phenyl. Examples of substituents which may be present on an aryl group include one or more of halogen, amino, nitro, alkyl, haloalkyl, alkoxy, phenoxy and phenoxy substituted by one or more of halo, alkyl or alkoxy. Preferred groups include alkyl such as methyl, ethyl or propyl, halo and haloalkyl groups such as trifluoromethyl or dichloroethyl.

A heteroaryl group or moiety may be for example an optionally substituted 5- or 6-membered heterocyclic aromatic ring which may contain from 1 to 4 heteroatoms selected from O, N or S. The heterocyclic ring may optionally be fused to a phenyl ring. Examples of heteroaryl groups thus include furyl, thienyl, pyrrolyl, oxazolyl, oxazinyl, thiazolyl, imidazolyl, oxadiazolyl, thiadiazolyl, pyridyl, triazolyl, triazinyl, pyridazyl, pyrimidinyl, pyrazolyl, indolyl, indazolyl, isoxazolyl, benzofuranyl, benzothienyl, benzimidazolyl, benzoxazolyl, benzoxazinyl, quinoxalinyl, quinolinyl, quinazolinyl, cinnolinyl, benzothiazolyl and pyridopyrrolyl. Preferably the heteroaryl group is pyridyl, thienyl, furyl or pyrrolyl. Suitable substitutents include one or more of halogen, amino, nitro alkyl, haloalkyl, alkoxy, or aryloxy. Preferred subsitutents are alkoxy groups such as hydroxy, methoxy or ethyloxy, most preferably hydroxy. The heteroaryl group or moiety may be fully or partially reduced. For the purposes of this invention the terms 'reduced' or 'reduction' relate to the addition of one or more electrons to an atom or the addition of hydrogen to a moiety. Examples of such reduced heteroaryl groups or moieties include any fully or partially saturated derivative of the aforementioned heteroaryl groups and include pyrrolidinyl, tetrahydrofuranyl, tetrahydrothienyl and piperidinyl groups.

A halo or halogen group is one or more of fluoride, chloride, bromide or iodide. An amino group is one or more of $NH_2$, $NHR^{21}$, $NR^{21}R^{22}$ or a salt thereof for example $NH_3Cl$. $R^{21}$ and $R^{22}$ are independently selected from $C_{1-30}$alkyl, preferably $C_{1-20}$alkyl or $C_{6-12}$aryl.

Haloalkyl groups are straight chain or branched alkyl groups as previously defined substituted with one or more halogen group wherein a halogen group is fluoride, chloride, bromide or iodide. Examples of haloalkyl group include trifluoromethyl and dichloroethyl.

Alkoxyl groups are straight or branched chain alkyl groups as previously defined wherein the alkyl chain is interrupted with one or more oxygen atom. Examples of alkoxy groups include methyoxy and ethoxy groups.

Aryloxy groups are aryl groups as previously defined wherein the aryl group is substituted with one or more oxygen atoms. Examples of aryloxy groups include phenoxy and phenylphenoxy groups.

In a more preferred feature of the first aspect, the invention provides the use of a compound of formula II

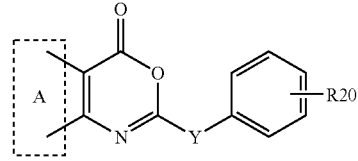

(II)

or a pharmaceutically acceptable salt, ester, amide or prodrug thereof, in the manufacture of a medicament for the prevention or treatment of obesity or an obesity-related disorder;

wherein group A is as defined for formula (I); preferably, the thienyl group A is optionally substituted with one or more of alkyl, aryl, halo, alkoxy, haloalkyl, aryloxy, amino, heteroaryl, or arylalkyl. More preferably the thienyl moiety A is optionally substituted with one or more of hydrogen, branched or unbranched alkyl having 1 to 10 carbon atoms, cyclic alkyl having 3 to 10 carbon atoms, aryl having 6 to 12 carbon atoms, haloalkyl having 1 to 10 carbon atoms, or a halogen;

Y is as defined for formula (I); preferably O, S or $NR_2$, wherein $R^2$ is preferably hydrogen, methyl, ethyl or propyl, most preferably hydrogen;

$R^{20}$ preferably represents a group selected from $OR^{13}$, $SR^{13}$, $SOR^{13}$, $—COR^{13}$, $CO_2R^{13}$, $SO_2R^{13}$, $CONR^{13}R^{14}$, $NR^{14}C(O)NR^{13}$, $C_{1-10}$alkyl, $C_{1-10}$alkoxy, $haloC_{1-10}$alkyl, cyano, halo, aryl, aryl $C_{1-10}$alkyl, heteroaryl or heteroaryl $C_{1-10}$alkyl;

wherein $R^{13}$ and $R^{14}$ each independently represents hydrogen, $C_{1-10}$alkyl, $C_{2-10}$alkenyl, $C_{1-10}$alkynyl, $C_{3-6}$cycloalkyl, $C_{3-6}$cycloalkenyl, aryl, aryl$C_{1-10}$alkyl, heteroaryl, heteroaryl$C_{1-10}$alkyl, reduced heteroaryl or reduced heteroaryl$C_{1-10}$alkyl;

wherein the alkyl, aryl, heteroaryl, alkenyl, alkynyl, cycloalkyl or cycloalkenyl can be optionally substituted with one or more of halo, $C_{1-10}$alkyl, $C_{1-10}$alkylhalo, $C_{1-10}$alkoxy, $C_{6-12}$aryl, $C_{1-10}$alkyl$C_{6-12}$aryl, $C_{6-12}$aryloxy, amino, hydroxy, nitro, $C_{5-12}$heteroaryloxy or $C_{5-12}$heteroaryl.

More preferably $R^{20}$ represents phenyloxy, phenylthio, SO-phenyl, $SO_2$-phenyl, alkylphenyl, CO-phenyl, $CO_2$-phenyl, $CONR^{14}$-phenyl, $NR^{14}CO$-phenyl or $NR^{14}$-phenyl optionally substituted with one or more of halo, $C_{1-10}$alkyl, $C_{1-10}$alkylhalo, $C_{1-10}$alkoxy, $C_{6-12}$aryl, $C_{1-10}$alkyl$C_{6-12}$aryl, $C_{6-12}$aryloxy, amino, hydroxy, nitro, $C_{5-12}$heteroaryloxy or $C_{5-12}$heteroaryl. Most preferably $R^{20}$ is phenyloxy, phenylthio, $CH_2$-phenyl or CO-phenyl, optionally substituted with one or more of halo, $C_{1-10}$alkyl, $C_{1-10}$alkylhalo, $C_{1-10}$alkoxy, $C_{6-12}$aryl, $C_{1-10}$alkyl$C_{6-12}$aryl, $C_{6-12}$aryloxy, amino, hydroxy, nitro, $C_{5-12}$heteroaryloxy or $C_{5-12}$heteroaryl. Preferably the substituent is one or more of alkyl for example methyl, ethyl, n-propyl or iso-propyl, halogen or alkylhalo for example trifluoromethyl or dichloroethyl.

The $R^{20}$ group can be located ortho, meta or para on the phenyl ring to group Y. Preferably, the group $R^{20}$ is para to group Y.

The invention provides the use of a compound of formula (I) or (II) as defined herein above, or a pharmaceutically acceptable salt, ester, amide or prodrug thereof, in the manufacture of a medicament for the control, prevention or treatment of obesity, or an obesity-related disorder.

For the purposes of this invention, obesity-related disorders include hyperlipaemia, hyperlipidaemia, hyperglycaemia (type II) diabetes), hypertension, cardiovascular disease, stroke, gastrointestinal disease and gastrointestinal conditions. The obesity-related disorder may be associated with the obese state of the patient. Alternatively, the obesity-related disorder may arise due to the genetic disposition of the patient, to environmental conditions or to other factors. Without being bound by scientific theory, it is proposed that for such a disorder not associated with the obese state of the patient, the use of the compounds of the present application will prevent or treat these diseases by causing the patients to lose weight. Such loss of weight may result in the amelioration or lessening of the symptoms of the above disorders.

The compounds of the present invention are particularly useful for the treatment of hyperglycaemia (type II diabetes). Hyperglycaemia is due to variable combinations of insulin resistance and islet B-cell failure. Although circulatory insulin levels may not be greatly reduced and may even be above the non-diabetic range, they are inadequate to overcome tissue insulin resistance. Hyperglycaemia is understood to have a number of possible causes. One of the most importance of these causes relates to obesity. The combination of a high intake of energy-rich fatty foods and physical inactivity has led to an increase in obesity with a corresponding increase in insulin resistance and hyperglycaemia, particularly in countries which have a 'westernised' lifestyle. By reducing the weight of a subject, the insulin resistance can be overcome, allowing a reduction or treatment of the symptoms of hyperglycaemia. A preferred feature of the present invention is therefore the use of a compound of formula (I) or (II) as defined herein above, or a pharmaceutically acceptable salt, ester, amide or prodrug thereof, in the manufacture of a medicament for the prevention or treatment of hyperglycaemia (type II diabetes).

Throughout this text, the prevention and/or treatment of any disorder means any effect which mitigates any damage or any medical disorder, to any extent, and includes prevention and treatment themselves as well as control of disease. The term "treatment" means any amelioration of disorder, disease, syndrome, condition, pain or a combination of two or more thereof. The term "control" means to prevent the condition from deteriorating or getting worse for example by halting the progress of the disease without necessary ameliorating the condition.

The invention further provides the use of a compound of formula (I) or (II), as defined herein above, or a pharmaceutically acceptable salt, ester, amide or prodrug thereof in the manufacture of a medicament for the inhibition of an enzyme involved in the metabolism or degradation of a fat (including a lipid or lipids), for example a lipase, a phosphatase or an esterase. Preferably the invention provides a compound of formula (I) and/or (II) as defined herein above, or a pharmaceutically acceptable salt, ester, amide or prodrug thereof in the manufacture of a medicament for the inhibition of a lipase enzyme, more preferably wherein the lipase enzyme is involved in the metabolism or degradation of a fat.

The first aspect of the invention further provides the use of a compound of formula (I) or (II), as defined herein above, or a pharmaceutically acceptable salt, ester, amide or prodrug thereof in the manufacture of a medicament for the inhibition of an enzyme whose preferred mode of action is to catalyse the hydrolysis of an ester functionality.

In a second aspect, the present invention provides a compound of formula (Ia)

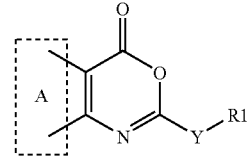

or a pharmaceutically acceptable salt, ester, amide or prodrug thereof;

wherein in formula (Ia), A is an optionally substituted thienyl moiety, with the thienyl moiety fused to the oxazinone ring in the 2,3-position, 3,4-postion or the 3,2-position as illustrated below;

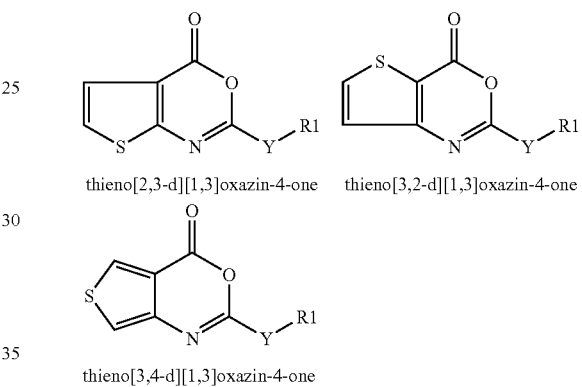

thieno[2,3-d][1,3]oxazin-4-one    thieno[3,2-d][1,3]oxazin-4-one thieno[3,4-d][1,3]oxazin-4-one preferably the thienyl moiety is fused to the oxazinone ring in the 2,3-position or the 3,2-position.

Y is O, S, or $NR^2$, wherein $R^2$ is hydrogen or alkyl;

and $R^1$ is alkyl, or aryl substituted with one or more of halogen, amino, nitro, cyano, aryl, alkylaryl, alkyl, haloalkyl, alkoxy, or with one or more optionally substituted aryloxy, arylthio, SO-aryl, $SO_2$-aryl alkylaryl, CO-aryl, $CO_2$-aryl, $CONR^6$-aryl, $NR^6CO$-aryl or $NR^6$-aryl;

wherein for the groups $R^1$, $R^2$ and $R^6$, preferably the alkyl groups have from 1 to 30 carbon atoms, the alkenyl groups have 2 to 30 carbon atoms, the alkynyl groups have 2 to 30 carbon atoms, the cycloalkyl groups have 3 to 30 carbon atoms, the cycloalkenyl groups have 3 to 30 carbon atoms, the aryl groups have 6 to 12 carbon atoms and the heteroaryl groups have 5 to 12 atoms.

In a preferred feature of the second aspect, the thienyl group A is optionally substituted with one or more of alkyl, aryl, halo, alkoxy, haloalkyl, aryloxy, amino, heteroaryl, or arylalkyl. More preferably the thienyl moiety A is optionally substituted with one or more of hydrogen, branched or unbranched alkyl having 1 to 20 carbon atoms, preferably 1 to 15 carbon atoms, cyclic alkyl having 3 to 10 carbon atoms, aryl having 6 to 12 carbon atoms, preferably phenyl, alkylaryl, haloalkyl, or a halogen. Most preferably, the thienyl group is substituted with one or more of halogen, alkyl or aryl. The thienyl group fused in the 2,3-position or the 3,2-position can be substituted at the 5- and/or 6-position. Preferably, the thienyl group is substituted at the 6-position. The thienyl group may alternatively be fused to a six-membered aryl, heterocycyl, or cycloalkyl ring preferably to a phenyl, cyclohexyl or pyridyl ring.

Y is O, S or $NR^2$; wherein $R^2$ is preferably hydrogen or an alkyl having 1 to 6 carbon atoms, more preferably methyl, ethyl or propyl;

$R^1$ is preferably a) an unbranched alkyl group having from 4 to 25 carbon atoms, a branched alkyl group having from 4 to 25 carbon atoms or an arylalkyl group wherein the alkyl moiety has from 2 to 25 carbon atoms; in particular, $R^1$ is an unbranched alkyl with 8, 9, 10, 11, 12, 13, 14, 15, 16, 17, 18, 19 or 20 carbon atoms, a branched alkyl group with 6, 7, 8, 9, 10, 11, 12, 13, 14, 15, 16, 17, 18, 19 or 20 carbon atoms or an arylalkyl group wherein the alkyl group has 4, 5, 6, 7, 8, 9, 10, 11, or 12 carbon atoms and the aryl group is preferably phenyl. The alkyl group can be substituted with one or more of aryl, halo, $CO_2R^{21}$, alkyl, alkynyl, alkenyl haloalkyl, heteroaryl, cyano, nitro, wherein $R^{21}$ is hydrogen, alkyl, aryl or $NR^6$.

b) a phenyl group substituted with one or more optionally substituted phenyloxy, phenylthio, SO-phenyl, $SO_2$-phenyl, alkylphenyl, CO-phenyl, $CO_2$-phenyl, $CONR^{16}$-phenyl, $NR^{16}CO$-phenyl or $NR^{16}$-phenyl; wherein the alkyl group is preferably an unbranched alkyl group having from 1 to 4 carbon atoms and R is preferably hydrogen, or an alkyl group such as methyl, ethyl, n-propyl or i-propyl; wherein the phenyloxy, phenylthio, SO-phenyl, $SO_2$-phenyl, alkylphenyl, CO-phenyl, $CO_2$-phenyl, $NR^{16}CO$-phenyl, $CONR^{16}$-phenyl or $NR^{16}$-phenyl groups are optionally substituted with one or more of halo, cyano, nitro, alkyl, alkylhalo, alkoxy, aryl, alkylaryl, aryloxy, amino, hydroxy or heteroaryl.

c) a phenyl group substituted with one or more of halo, $NR^6R^7$, $OR^6$, $SR^6$, $COR^6$, $CO_2R^6$, nitro, cyano, aryl, heteroaryl, alkylaryl, alkyl, haloalkyl, or alkoxy. The phenyl group can be substituted at the ortho, meta or para position. Preferably, the phenyl group is substituted at the meta or para position. Preferred options for $R^1$ include cyanosubstituted phenyl, alkoxysubstituted phenyl, and halosubstituted phenyl.

In a more preferred feature of the second aspect, the invention provides a compound of formula IIa

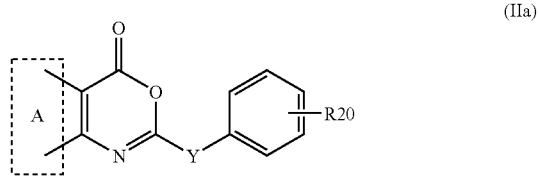

(IIa)

or a pharmaceutically acceptable salt, ester, amide or prodrug thereof;

wherein group A is as defined for formula (Ia), preferably a thienyl moiety optionally substituted with one or more of halogen $C_{1-10}$ branched or straight chain alkyl or aryl;

Y is as defined for formula (Ia), preferably O, S or NH;

And $R^{20}$ is optionally substituted phenyloxy, phenylthio, SO-phenyl, $SO_2$-phenyl, alkylphenyl, CO-phenyl, $CO_2$-phenyl, $CONR^6$-phenyl, $NR^6CO$-phenyl or $NR^6$-phenyl, preferably $R^{20}$ is phenyloxy, phenylthio, $CH_2$-phenyl or CO-phenyl optionally substituted with one or more of halo, cyano, alkyl, alkylhalo, alkoxy, aryl, alkylaryl, aryloxy, amino, hydroxy or heteroaryl. Preferably the substituent is one or more of alkyl for example methyl, ethyl, n-propyl or iso-propyl, halogen for example chlorine or bromine or alkylhalo for example trifluoromethyl or dichloroethyl.

The $R^{20}$ group can be located ortho, meta or para on the phenyl ring to group Y. Preferably, the group $R^{20}$ is para to group Y. The phenyl group comprising the group $R^{20}$ can be substituted at the ortho, meta or para position, preferably the phenyl group is substituted at the meta or para positions;

Representative compounds according to the first and/or second aspects of the invention are those which include:

TABLE 1

| Reference Number | Structure | Compound Name |
| --- | --- | --- |
| 1 | 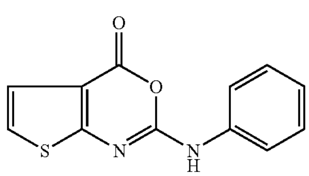 | 2-Phenylamino-4H-thieno[2,3-d][1,3]oxazin-4-one |
| 2 | 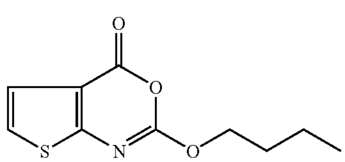 | 2-Butyloxy-4H-thieno-[2,3-d][1,3]oxazin-4-one |
| 3 | 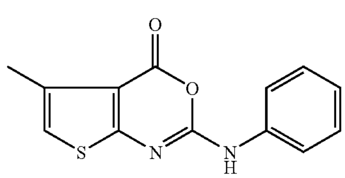 | 5-Methyl-2-phenylamino-4H-thieno[2,3-d][1,3]oxazin-4-one |

TABLE 1-continued

| Reference Number | Structure | Compound Name |
|---|---|---|
| 4 | 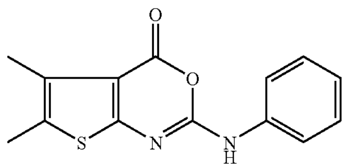 | 5,6-Dimethyl-2-phenylamino-4H-thieno[2,3-d][1,3]oxazin-4-one |
| 5 | 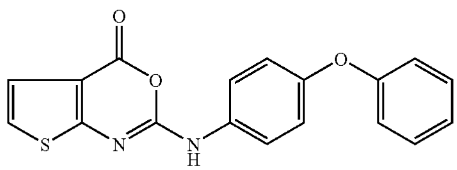 | 2-(4-Phenoxy)phenylamino-4H-thieno[2,3-d][1,3]oxazin-4-one |
| 6 | 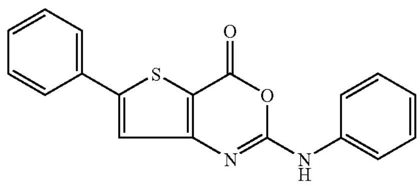 | 5-Phenyl-2-phenylamino-4H-thieno[3,2-d][1,3]oxazin-4-one |
| 7 | 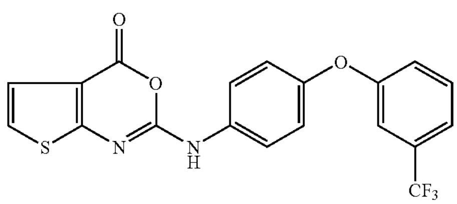 | 2-(4-(3-Trifluoromethyl-phenoxy)phenylamino)-4H-thieno[2,3-d][1,3]oxazin-4-one |
| 8 | 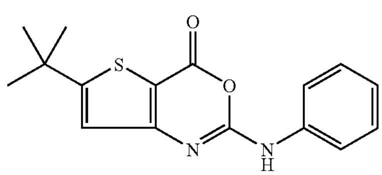 | 5-(1,1-Dimethylethyl)-2-phenylamino-4H-thieno[3,2-d][]1,3]oxazin-4-one |
| 9 | 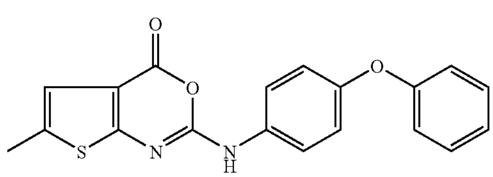 | 6-Methyl-2-(4-phenoxy)phenylamino-4H-thieno[2,3-d][1,3]oxazin-4-one |
| 10 | 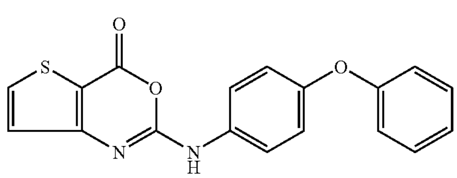 | 2-(4-Phenoxy)phenylamino-4H-thieno[3,2-d][1,3]oxazin-4-one |
| 11 | 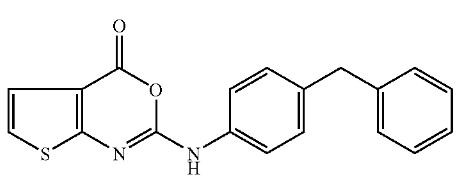 | 2-(4-Phenylmethyl)phenylamino-4H-thieno[2,3-d][1,3]oxazin-4-one |

TABLE 1-continued

| Reference Number | Structure | Compound Name |
|---|---|---|
| 12 | 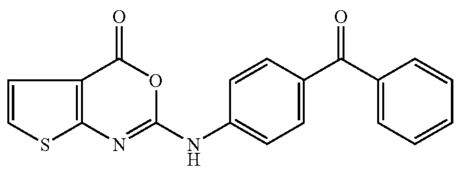 | 2-(4-Benzoyl)phenylamino-4H-thieno[2,3-d][1,3]oxazin-4-one |
| 13 | 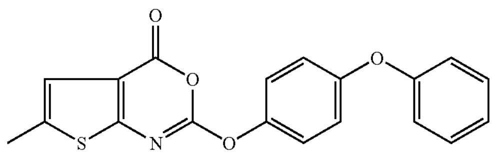 | 6-Methyl-2-(4-phenoxy)phenoxy-4H-thieno[2,3-d][1,3]oxazin-4-one |
| 14 | 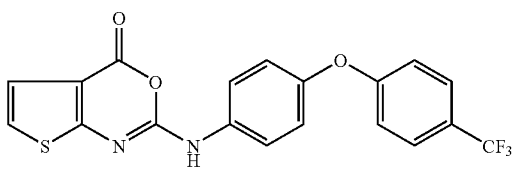 | 2-(4-(4-Trifluoromethyl-phenoxy)phenylamino)-4H-thieno[2,3-d][1,3]oxazin-4-one |
| 15 | 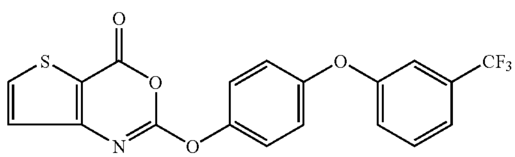 | 2-(4-(3-Trifluoromethyl-phenoxy)phenoxy)-4H-thieno[3,2-d][1,3]oxazin-4-one |
| 16 | 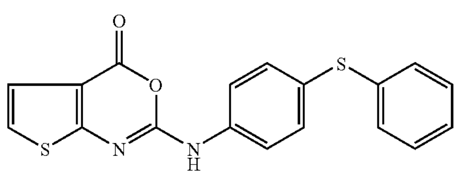 | 2-(4-Phenylthio)phenylamino-4H-thieno[2,3-d][1,3]oxazin-4-one |
| 17 | 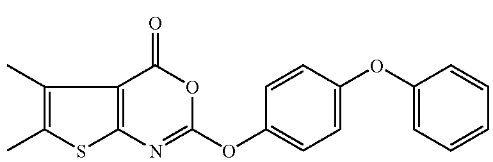 | 5,6-Dimethyl-2-(4-phenoxy)phenoxy-4H-thieno[2,3-d][1,3]oxazin-4-one |
| 18 | 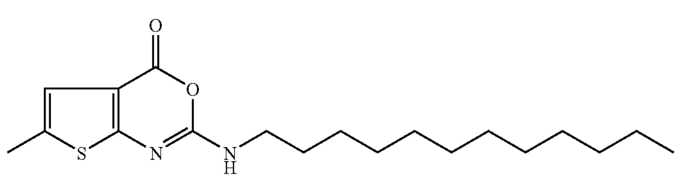 | 2-Dodecylamino-6-methyl-4H-thieno[2,3-d][1,3]oxazin-4-one |
| 19 | 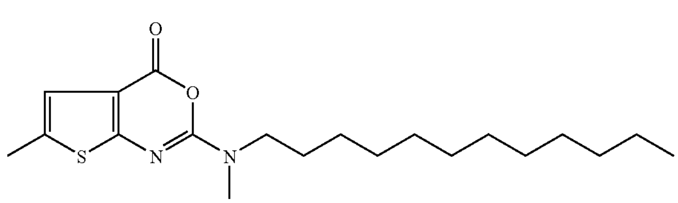 | 2-N-Dodecyl-N-methylamino-6-methyl-4H-thieno[2,3-d][1,3]oxazin-4-one |

TABLE 1-continued

| Reference Number | Structure | Compound Name |
|---|---|---|
| 20 | 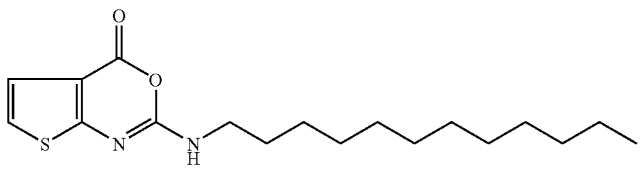 | 2-Dodecylamino-4H-thieno[2,3-d][1,3]oxazin-4-one |
| 21 | 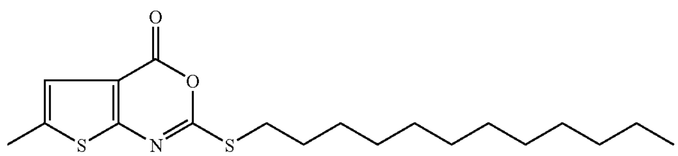 | 2-Dodecylthio-6-methyl-4H-thieno[2,3-d][1,3]oxazin-4-one |
| 22 | 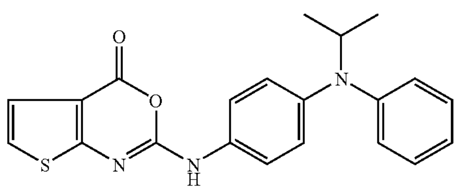 | 2-(4-N-(1-Methylethyl)-N-phenylamino)phenylamino-4H-thieno[2,3-d][1,3]oxazin-4-one |
| 23 | 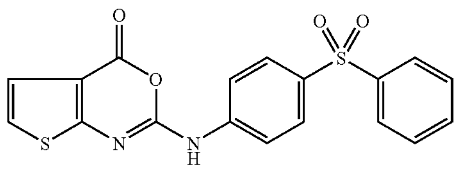 | 2-(4-Phenylsulfonyl)phenylamino-4H-thieno[2,3-d][1,3]oxazin-4-one |
| 24 | 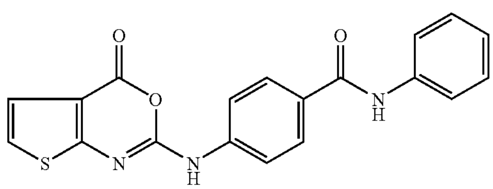 | 2-(4-Phenylcarbamoyl)phenylamino-4H-thieno[2,3-d][1,3]oxazin-4-one |
| 25 | 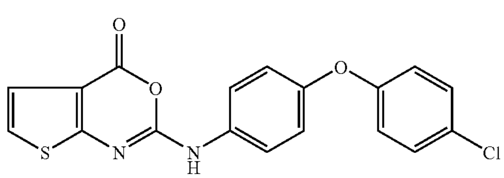 | 2-(4-(4-Chlorophenoxy)-phenylamino)-4H-thieno[2,3-d][1,3]oxazin-4-one |
| 26 | 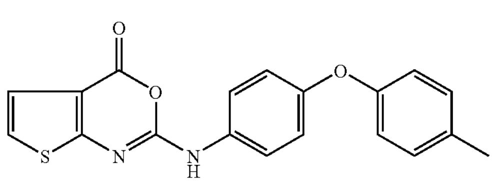 | 2-(4-(4-Methylphenoxy)-phenylamino)-4H-thieno[2,3-d][1,3]oxazin-4-one |
| 27 | 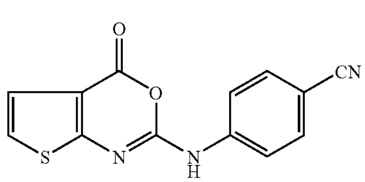 | 2-(4-Cyanophenyl)amino-4H-thieno[2,3-d][1,3]oxazin-4-one |

TABLE 1-continued

| Reference Number | Structure | Compound Name |
|---|---|---|
| 28 | 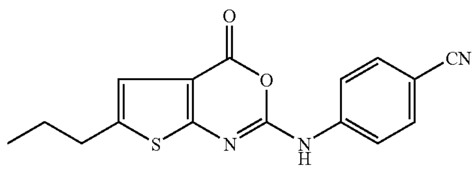 | 2-(4-Cyanophenyl)amino-6-propyl-4H-thieno[2,3-d][1,3]oxazin-4-one |
| 29 | 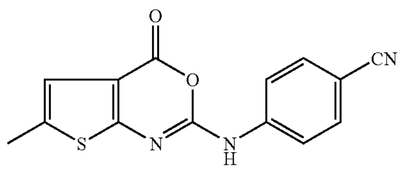 | 2-(4-Cyanophenyl)amino-6-methyl-4H-thieno[2,3-d][1,3]oxazin-4-one |
| 30 | 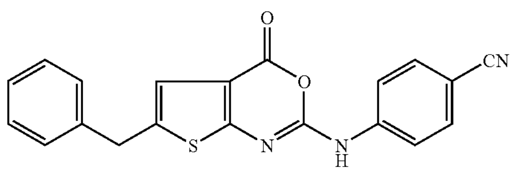 | 6-Phenylmethyl-2-(4-cyanophenyl)amino-4H-thieno[2,3-d][1,3]oxazin-4-one |
| 31 | 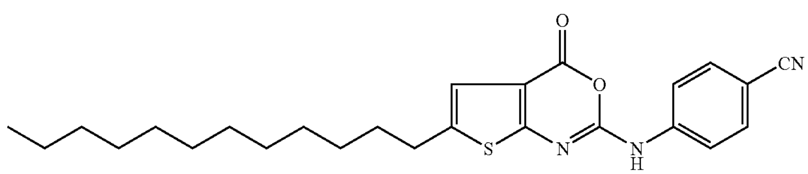 | 2-(4-Cyanophenyl)amino-6-dodecyl-4H-thieno[2,3-d][1,3]oxazin-4-one |
| 32 | 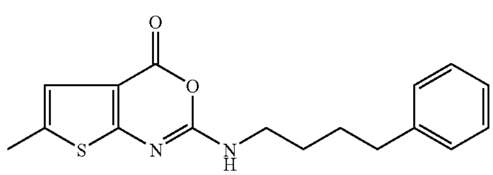 | 6-Methyl-2-(4-phenylbutyl)amino-4H-thieno[2,3-d][1,3]oxazin-4-one |
| 33 | 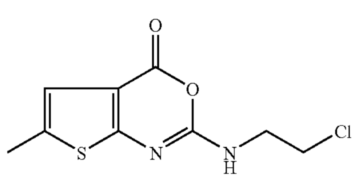 | 2-(2-Chloroethyl)amino-6-methyl-4H-thieno[2,3-d][1,3]oxazin-4-one |
| 34 | 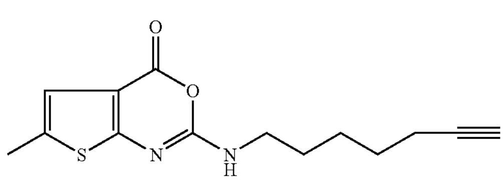 | 2-(Hept-6-enyl)amino-6-methyl-4H-thieno[2,3-d][1,3]oxazin-4-one |
| 35 | 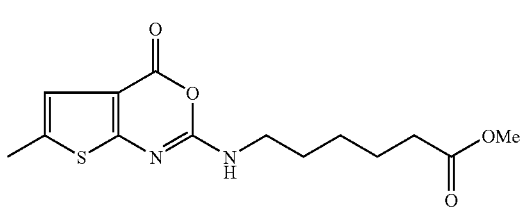 | 2-(5-Methoxycarbonylpentyl)amino-6-methyl-4H-thieno[2,3-d][1,3]oxazin-4-one |

TABLE 1-continued

| Reference Number | Structure | Compound Name |
|---|---|---|
| 36 | 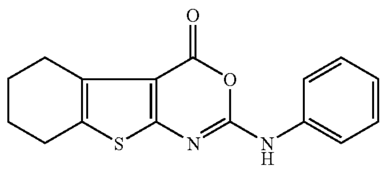 | 2-Phenylamino-5,6,7,8-tetrahydro-4H-benzothieno[2,3-d][1,3]oxazin-4-one |
| 37 | 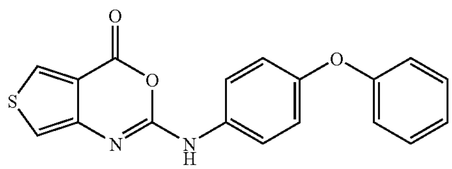 | 2-(4-Phenoxy)phenylamino-4H-thieno-[3,4-d][1,3]oxazin-4-one |
| 38 | 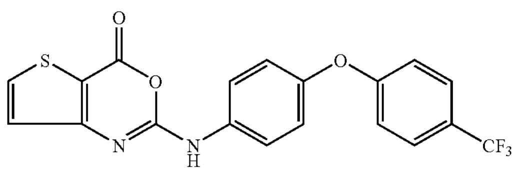 | 2-(4-(4-Trifluoromethyl-phenoxy)phenylamino)-4H-thieno[3,2-d][1,3]oxazin-4-one |
| 39 | 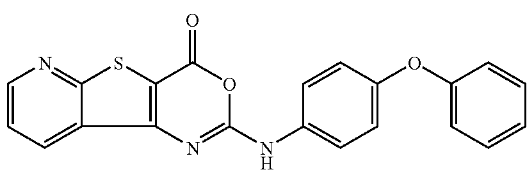 | 6-(4-Phenoxyphenylamino)-7-oxa-9-thia-1,5-diazafluoren-8-one |
| 40 | 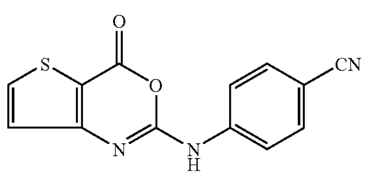 | 2-(4-Cyanophenyl)amino-4H-thieno[3,2-d][1,3]oxazin-4-one |
| 41 | 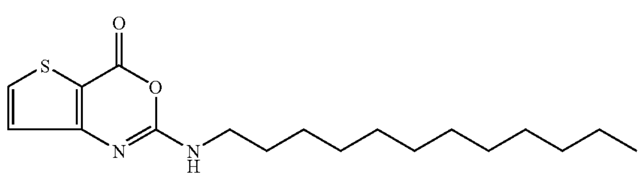 | 2-Dodecylamino-4H-thieno[3,2-d][1,3]oxazin-4-one |
| 42 | 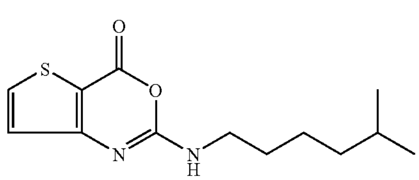 | 2-(5-Methylhexyl)amino-4H-thieno[3,2-d][1,3]oxazin-4-one |
| 43 | 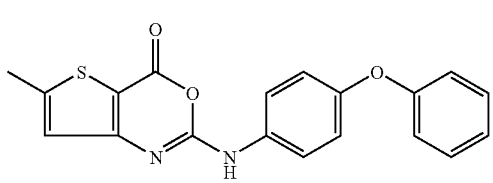 | 5-Methyl-2-(4-phenoxy)phenylamino-4H-thieno[3,2-d][1,3]oxazin-4-one |

TABLE 1-continued

| Reference Number | Structure | Compound Name |
|---|---|---|
| 44 | 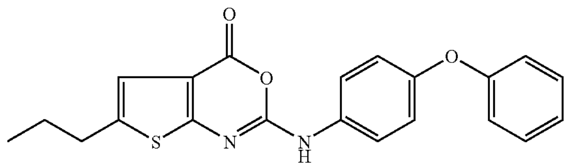 | 6-Propyl-2-(4-phenoxy)phenylamino-4H-thieno[2,3-d][1,3]oxazin-4-one |
| 45 | 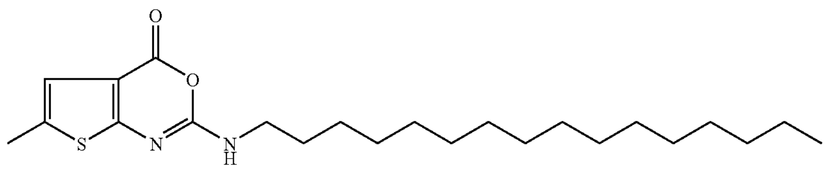 | 2-Hexadecylamino-6-methyl-4H-thieno-[2,3-d][1,3]oxazin-4-one |
| 46 | 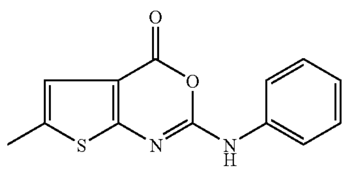 | 6-Methyl-2-phenylamino-4H-thieno[2,3-d][1,3]oxazin-4-one |
| 47 | 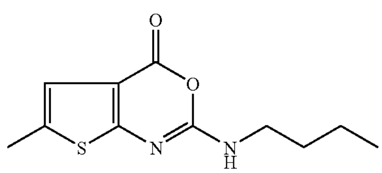 | 2-Butylamino-6-methyl-4H-thieno[2,3-d][1,3]oxazin-4-one |
| 48 | 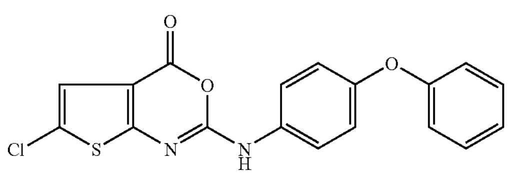 | 6-Chloro-2-(4-phenoxy)phenylamino-4H-thieno[2,3-d][1,3]oxazin-4-one |
| 49 | 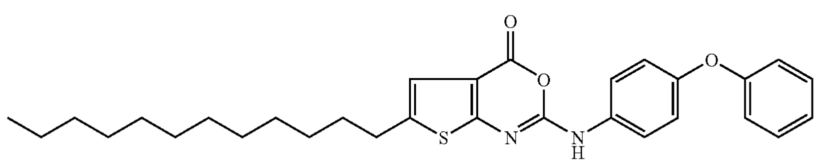 | 6-Dodecyl-2-(4-phenoxy)phenylamino-4H-thieno[2,3-d][1,3]oxazin-4-one |
| 50 | 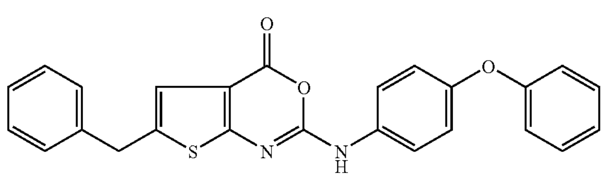 | 6-Phenylmethyl-2-(4-phenoxy)phenylamino-4H-thieno[2,3-d][1,3]oxazin-4-one |
| 51 | 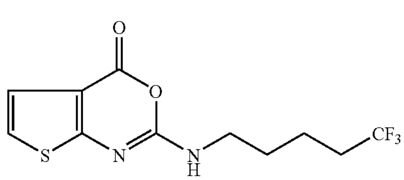 | 2(5,5,5-Trifluoropentyl)amino-4H-thieno[2,3-d][1,3]oxazin-4-one |
| 52 | 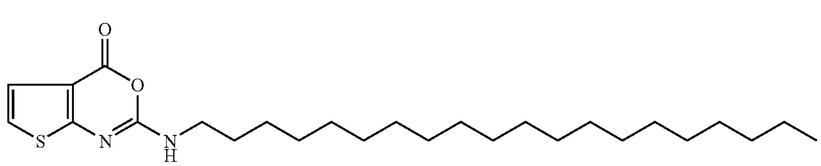 | 2-Eicosylamino-4H-thieno[2,3-d][1,3]oxazin-4-one |

TABLE 1-continued

| Reference Number | Structure | Compound Name |
|---|---|---|
| 53 | 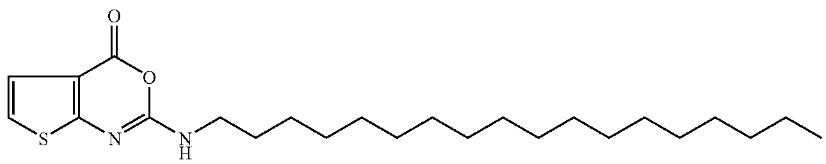 | 2-Octadecylamino-4H-thieno[2,3-d][1,3]oxazin-4-one |
| 54 | 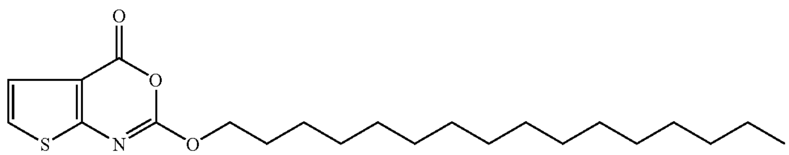 | 2-Hexadecyloxy-4H-thieno[2,3-d][1,3]oxazin-4-one |
| 55 | 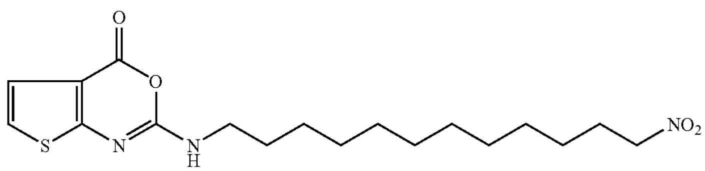 | 2-(12-Nitrododecyl)-amino-4H-thieno[2,3-d][1,3]oxazin-4-one |
| 56 | 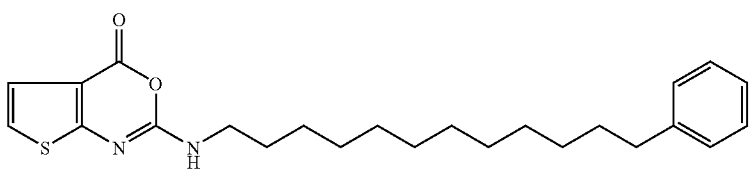 | 2-(12-Phenyldodecyl)-amino-4H-thieno[2,3-d][1,3]oxazin-4-one |
| 57 | 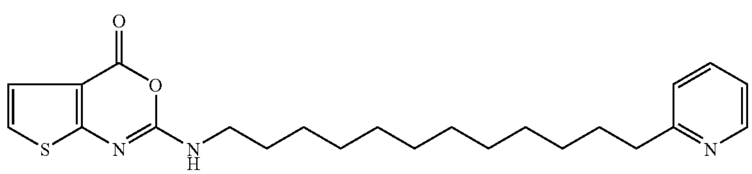 | 2-(12-(Pyrid-2-yl)dodecyl)-amino-4H-thieno[2,3-d][1,3]oxazin-4-one |
| 58 | 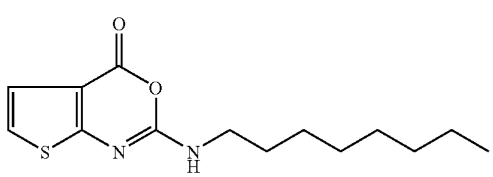 | 2-Octylamino-4H-thieno[2,3-d][1,3]oxazin-4-one |
| 59 | 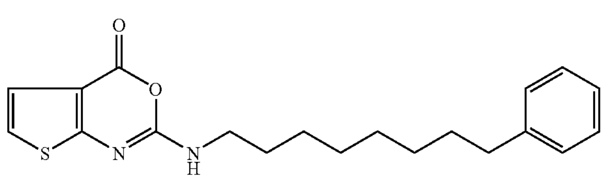 | 2-(8-Phenyloctyl)amino-4H-thieno[2,3-d][1,3]oxazin-4-one |
| 60 | 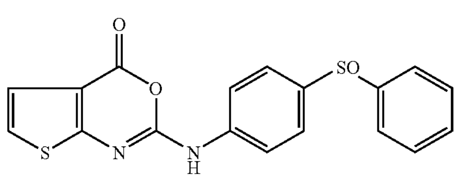 | 2-(4-Phenylsulfinyl)-phenylamino-4H-thieno[2,3-d][1,3]oxazin-4-one |

TABLE 1-continued

| Reference Number | Structure | Compound Name |
| --- | --- | --- |
| 61 | 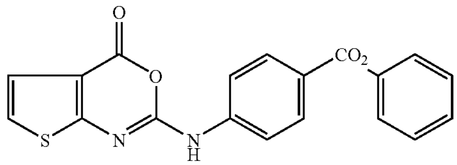 | 2-(4-Phenoxycarbonyl)-phenylamino-4H-thieno[2,3-d][1,3]oxazin-4-one |
| 62 | 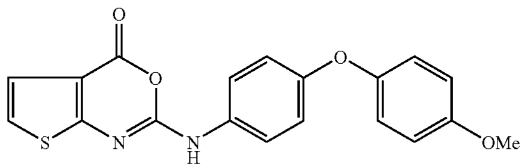 | 2(4-(4-Methoxyphenoxy)-phenylamino)-4H-thieno[2,3-d][1,3]oxazin-4-one |
| 63 | 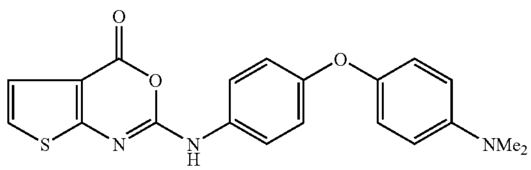 | 2(4-(4-Dimethylaminophenoxy)-phenylamino)-4H-thieno[2,3-d][1,3]oxazin-4-one |
| 64 | 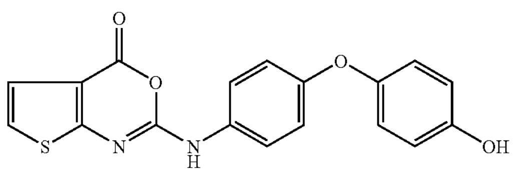 | 2(4-(4-Hydroxyphenoxy)-phenylamino)-4H-thieno[2,3-d][1,3]oxazin-4-one |
| 65 | 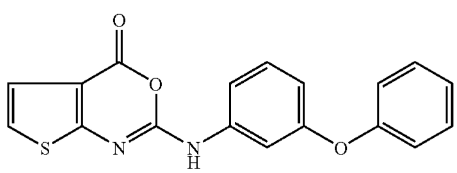 | 2(3-Phenoxy)-phenylamino-4H-thieno[2,3-d][1,3]oxazin-4-one |
| 66 | 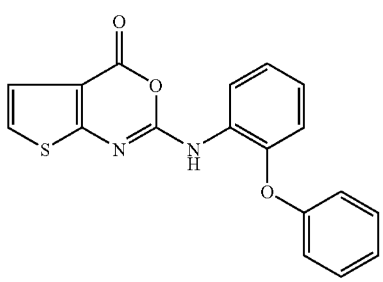 | 2(2-Phenoxy)-phenylamino-4H-thieno[2,3-d][1,3]oxazin-4-one |
| 67 | 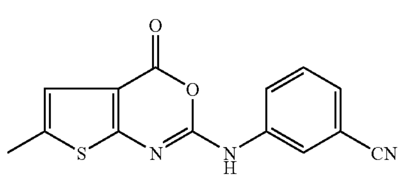 | 2-(3-Cyanophenyl)amino-6-methyl-4H-thieno[2,3-d][1,3]oxazin-4-one |
| 68 | 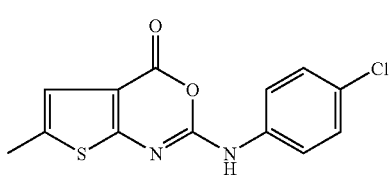 | 2-(4-Chlorophenyl)amino-6-methyl-4H-thieno[2,3-d][1,3]oxazin-4-one |

TABLE 1-continued

| Reference Number | Structure | Compound Name |
|---|---|---|
| 69 | 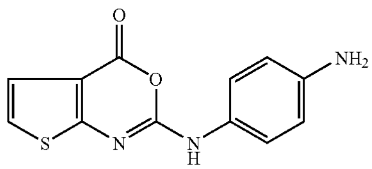 | 2-(4-Aminophenyl)-amino-4H-thieno[2,3-d][1,3]oxazin-4-one |
| 70 | 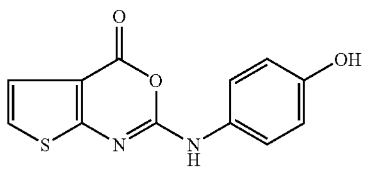 | 2-(4-Hydroxyphenyl)-amino-4H-thieno[2,3-d][1,3]oxazin-4-one |
| 71 | 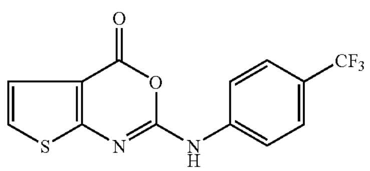 | 2-(4-Trifluoromethylphenyl)-amino-4H-thieno[2,3-d][1,3]oxazin-4-one |
| 72 | 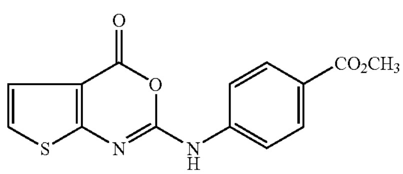 | 2-(4-Methyoxycarbonylphenyl)-amino-4H-thieno[2,3-d][1,3]oxazin-4-one |
| 73 | 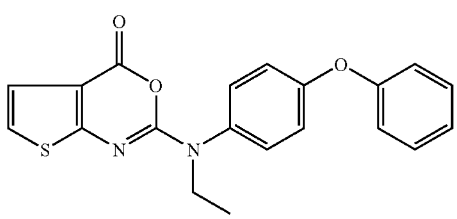 | 2-N-(4-Phenoxy)phenyl-N-ethylamino-4H-thieno[2,3-d][1,3]oxazin-4-one |
| 74 | 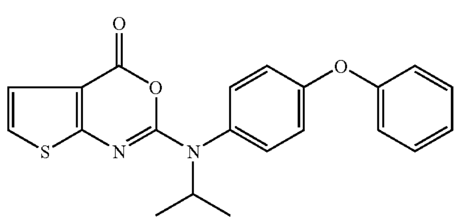 | 2-N-(4-Phenoxy)phenyl-N-1-methylethylamino-4H-thieno[2,3-d][1,3]oxazin-4-one |
| 75 | 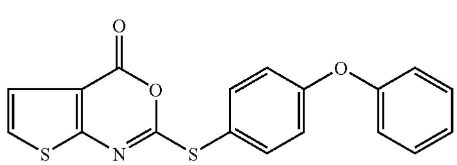 | 2-(4-Phenoxy)phenylthio-4H-thieno[2,3-d][1,3]oxazin-4-one |
| 76 | 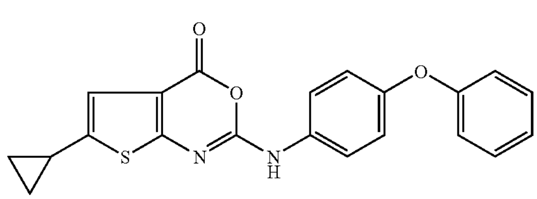 | 6-Cyclopropyl-2-(4-phenoxy)phenylamino-4H-thieno[2,3-d][1,3]oxazin-4-one |

TABLE 1-continued

| Reference Number | Structure | Compound Name |
| --- | --- | --- |
| 77 | 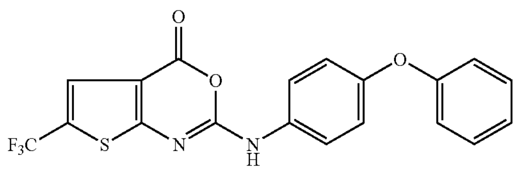 | 2-(4-Phenoxy)phenylamino-6-trifluoromethyl-4H-thieno[2,3-d][1,3]oxazin-4-one |
| 78 | 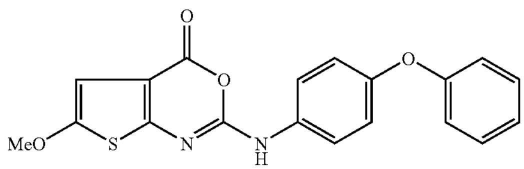 | 6-Methoxy-2-(4-phenoxy)phenylamino-4H-thieno[2,3-d][1,3]oxazin-4-one |
| 79 | 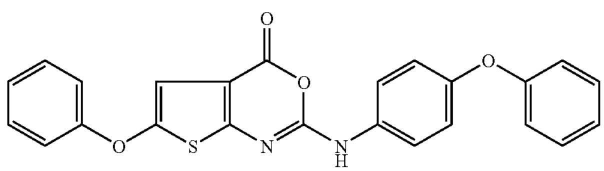 | 6-Phenoxy-2-(4-phenoxy)phenylamino-4H-thieno[2,3-d][1,3]oxazin-4-one |
| 80 | 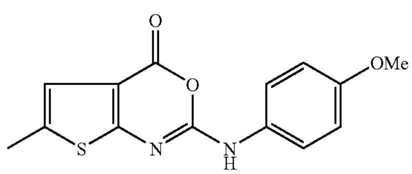 | 6-Methyl-2-(4-methoxyphenyl)-amino-4H-thieno[2,3-d][1,3]oxazin-4-one |
| 81 | 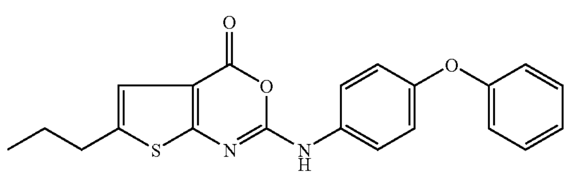 | 2-(4-Phenoxy)phenylamino-6-propyl-4H-thieno[2,3-d][1,3]oxazin-4-one |
| 82 | 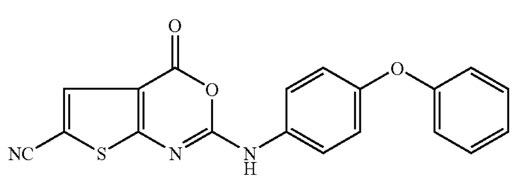 | 6-Cyano-2-(4-phenoxy)phenylamino-4H-thieno[2,3-d][1,3]oxazin-4-one |
| 83 | 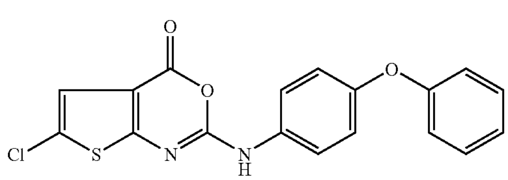 | 6-Chloro-2-(4-phenoxy)phenylamino-4H-thieno[2,3-d][1,3]oxazin-4-one |
| 84 | 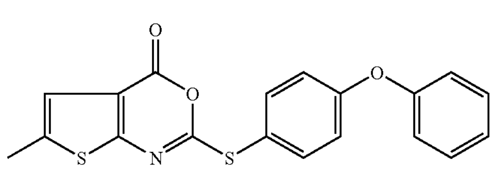 | 6-Methyl-2-(4-phenoxy)phenylthio-4H-thieno[2,3-d][1,3]oxazin-4-one |

TABLE 1-continued

| Reference Number | Structure | Compound Name |
|---|---|---|
| 85 | 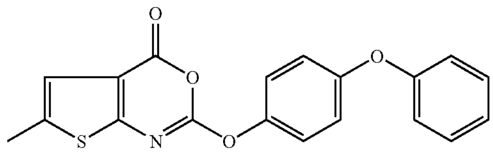 | 6-Methyl-2-(4-phenoxy)phenoxy-4H-thieno[2,3-d][1,3]oxazin-4-one |
| 86 | 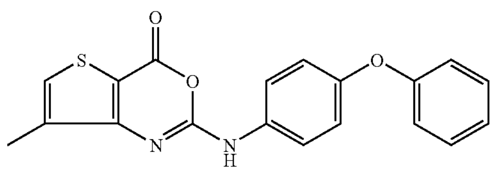 | 6-Methyl-2-(4-phenoxy)phenoxy-4H-thieno[3,2-d][1,3]oxazin-4-one |
| 87 | 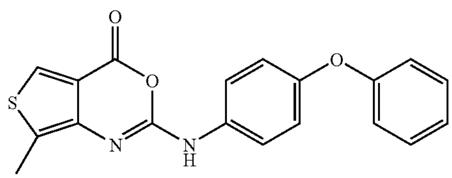 | 7-Methyl-2-(4-phenoxy)phenylamino-4H-thieno[3,4-d][1,3]oxazin-4-one. |
| 88 | 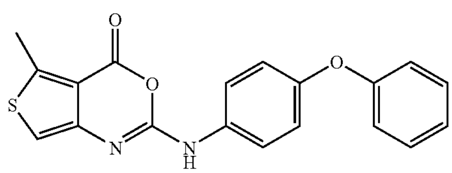 | 5-Methyl-2-(4-phenoxy)phenylamino-4H-thieno[3,4-d][1,3]oxazin-4-one |
| 89 | 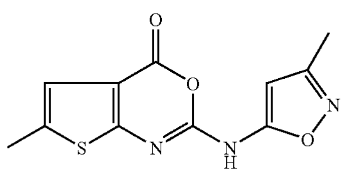 | 6-Methyl-2-(3-methylisoxazol-5-yl)amino-4H-thieno[2,3-d][1,3]oxazin-4-one |

Preferred compounds of the invention listed above extend to the tautomers thereof, as well as (but not limited to) pharmaceutically acceptable salts, esters, amides or prodrugs thereof or a derivative optionally with one or more lipid groups (natural or synthetic) attached.

The invention extends to prodrugs of the aforementioned compounds. A prodrug is any compound that may be converted under physiological conditions or by solvolysis to any of the compounds of the invention or to a pharmaceutically acceptable salt of the compounds of the invention. A prodrug may be inactive when administered to a subject but is converted in vivo to an active compound of the invention.

The compounds of the invention may contain one or more stereogenic (asymmetric) carbon atoms and may exist in racemic and optically active forms (enantiomers). The first aspect of the invention includes all such enantiomers and mixtures thereof, including racemic mixtures.

Examples of pharmaceutically acceptable salts of the compounds of formulae (I), (Ia), (II), and (IIa) include those derived from organic acids such as methanesulphonic acid, benzenesulphonic acid and p-toluenesulphonic acid, mineral acids such as hydrochloric and sulphuric acid and the like, giving methanesulphonate, benzenesulphonate, p-toluenesulphonate, hydrochloride and sulphate, and the like, respectively or those derived from bases such as organic and inorganic bases. Examples of suitable inorganic bases for the formation of salts of compounds for this invention include the hydroxides, carbonates, and bicarbonates of ammonia, lithium, sodium, calcium, potassium, aluminium, iron, magnesium, zinc and the like. Salts can also be formed with suitable organic bases. Such bases suitable for the formation of pharmaceutically acceptable base addition salts with compounds of the present invention include organic bases which are nontoxic and strong enough to form salts. Such organic bases are already well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; and the like.

Salts may be prepared in a conventional manner using methods well known in the art. Acid addition salts of said basic compounds may be prepared by dissolving the free base compounds according to the first or second aspects of the invention in aqueous or aqueous alcohol solution or other suitable solvents containing the required acid. Where a compound of formula (I), (Ia), (II), and (IIa) contain an acidic function a base salt of said compound may be prepared by reacting said compound with a suitable base. The acid or base salt may separate directly or can be obtained by concentrating the solution eg. by evaporation. The compounds of this invention may also exist in solvated or hydrated forms.

All preferred features of the second aspect also apply to the first aspect of the present invention.

A third aspect of the invention provides a process for the manufacture of any one or more of the novel compounds or derivatives according to the first or second aspects of the invention. Thus, the present invention provides a process for the preparation of a novel compound of formula (I), (Ia), (II), and/or (IIa) which process comprises:

Process (A) reacting a compound of formula (IV):

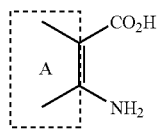

with a compound of formula (V):

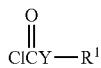

(V)

or

Process (B) cyclising a compound of formula (VI)

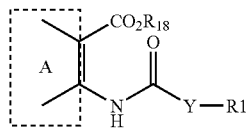

wherein $R^1$ is as hereinbefore defined and $R^{18}$ is hydrogen or $C_{1-6}$alkyl.

or:

Process (C) reacting a compound of formula (VII)

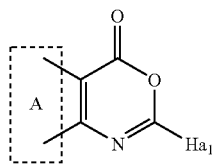

wherein $Ha_1$ is a halide, for example F, Cl, Br or I.

with a compound of formula (VIII):

 (VIII)

or:

Process (D): reacting a compound of formula (IX):

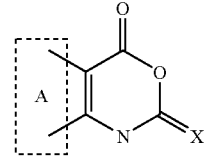

wherein X is O, S or NH with a compound of formula (X):

$ICH_2R^1$ (X)

Process (E) converting a compound of formula (I), (Ia), (II), and/or (IIa) into a different compound of formula (I), (Ia), (II), and/or (IIa), by, for example, (i) reduction of a compound of formula (I), (Ia), (II), and/or (IIa) wherein $R^1$ or $R^2$ or any substituent on the heterocyclic group A contains an alkenyl or alkynyl group or moiety, to the corresponding alkyl or alkenyl group or moiety; or (ii) alkylation of a compound of formula (I), (Ia), (II), and/or (IIa) where one or more substituent on the heterocyclic group A represents a halogen atom.

Process (A) may be effected by reacting a compound of formula (IV) with a compound of formula (V) wherein the compound of formula (V) may be a chlorothiolformate, a chloroformate or a carbamoyl chloride. In addition the compound of formula (V) may be replaced with an isocyanate. The process is preferably carried out under basic conditions, e.g. using pyridine. An excess (more than two equivalents) of the compound of formula (V) is employed, so that the intermediate carbamate initially formed is cyclised by reaction with the excess compound of formula (V).

Compounds of formula (V) for use in the process (A) may be prepared by standard methods well known in the art, e.g. by reaction of the corresponding thiol $R^1SH$, alcohol $R^1OH$ or amine $R^1R^2NH$ with phosgene.

Process (B) may be effected by reaction of a compound (VI) wherein $R^{18}$ is hydrogen, in the presence of a cyclisation reagent, e.g. an alkyl chloroformate, for example as described for process (A). Alternatively a compound (VI) may be cyclised by treatment with a dehydrating agent such as concentrated sulphuric acid.

Alternatively, compounds (VI) wherein $R^{18}$ is an alkyl group may be prepared by reacting an ester corresponding to formula (IV) with e.g. phosgene and a base such as pyridine to afford the corresponding isocyanate, followed by treatment with an alcohol, thiol or amine. If desired the ester (i.e. where $R^{18}$ is alkyl) may be hydrolysed to the corresponding acid ($R^{18}$=H) using for example lithium hydroxide in e.g. aqueous tetrahydrofuran or aqueous dioxane.

It will be appreciated that process (A) also proceeds via an intermediate of formula (VI) and is hence a variant of process (B).

Process (C) may be effected by reacting a compound of formula (VII) with a thiol, alcohol or amine of formula (VIII) in the presence of a base such as triethylamine.

Process (D) may be effected by reacting a compound of formula (IX) with an alkyl iodide and potassium carbonate in a solvent such as acetone.

A compound of formula (IX) may be prepared by cyclisation of a compound of formula (IV), with a phosgene, thiophosgene or cyanogen bromide. (See Krantz et al., *J. Med. Chem.* 1990, 33(2):464-479).

In process (E), reduction of an alkenyl or alkynyl group may be effected for example by catalytic hydrogenation using e.g. 10% palladium on charcoal in an alcoholic solvent, such as ethanol, under 1 atmosphere of hydrogen gas.

Alkylation according to process (E)(ii) may be effected using a Stille or other palladium catalysed cross-coupling process, using e.g. tetra-alkyl tin such as tetramethyl tin and PhCH$_2$Pd(PPh$_3$)$_2$Cl in HMPA at elevated temperature e.g. 50-100° C. Other halides or pseudohalides e.g. triflates may be employed as starting materials.

All preferred features of the first and second aspects also apply to the third aspect of the present invention.

A fourth aspect of the invention is a compound according to the first and/or second aspect of the invention (i.e. compounds of formulae (I), (Ia), (II), and/or (IIa)), for use in medicine. More preferably, the fourth aspect relates to a compound of the second aspect (i.e. compounds of formulae (Ia) and/or (IIa)) for use in medicine. Preferred features of the first and/or second aspects of the invention also apply to the fourth aspect. Further details of the fourth aspect of the invention are set out in the text which follows.

Compounds according to the invention, for use in medicine, are primarily for use in relation to the prevention and/or treatment of a medical condition such as obesity or an obesity-related disease such as hyperlipaemia, hyperlipidaemia, hyperglycaemia (type II diabetes), hypertension, cardiovascular disease, stroke, a gastrointestinal disease or a gastrointestinal condition. The invention also relates to non-medical weight loss, such as cosmetic weight loss and includes improving bodily appearance in general.

Compounds according to the first and second aspects of the invention are useful in these and other conditions due to their ability to inhibit an enzyme whose preferred mode of action is to catalyse the hydrolysis of an ester functionality (in vivo, as the enzyme naturally occurs). The fourth aspect therefore provides a compound as defined in the first and/or second aspects for the prevention or treatment of a condition which requires the inhibition of an enzyme whose preferred mode of action is to catalyse the hydrolysis of an ester functionality. Preferably the fourth aspect provides a compound as defined in the first or second aspects of the invention for the prevention or treatment of a condition which requires the inhibition of an enzyme involved in the metabolism or degradation of a fat.

Clearly, an important application of the invention is in relation to weight loss (of all kinds as described above) in humans. However, the invention also applies to medical and non-medical weight loss in any animal. In particular the invention applies to any animal whose metabolism of fat and fat derivatives involves an enzyme whose preferred mode of action is to catalyse the hydrolysis of an ester functionality (in vivo, as the enzyme naturally occurs). Thus, the invention has veterinary application and is particularly useful in relation to medical and non-medical weight loss in companion animals such as pet cats and dogs as well as in animals which provide meat for human consumption.

The loss of weight will provide a number of physiological and psychological benefits to a subject including but not limited to improved cardiovascular function, improved body image, reduced cholesterol levels and perceived or actual increase in energy. In addition, the loss of weight will provide a benefit in conditions which are caused by or exacerbated by obesity. Such conditions include hyperlipaemia, hyperlipidaemia, hyperglycaemia (type II diabetes), hypertension, cardiovascular disease, stroke, gastrointestinal disease and gastrointestinal conditions.

It is also believed that the compounds may be useful in reducing levels of toxins (e.g. dioxins and PCBs) stored in body fat. Without wishing to be bound by theory, it is believed that increasing the amount of undigested fat passing through the body enhances diffusion of toxins from fat stored in the body into fats in the blood, and thence into the intestine.

The fourth aspect of the invention further provides the use of compounds as defined in the first or second aspect of the invention in the manufacture of a medicament for the prevention or treatment of obesity or an obesity-related disorder. Preferably the fourth aspect provides the use of compounds as defined in the second aspect for this use.

All preferred features of the first, second and third aspects also apply to the fourth aspect of the present invention.

A fifth aspect of the invention relates to a compound according to the first and/or second aspects of the invention for use in the inhibition of an enzyme whose preferred mode of action is to catalyse the hydrolysis of an ester functionality. This includes both in vivo and in vitro uses and other uses such as industrial uses. Such an enzyme is one which catalyses the breakdown of a substrate containing an ester functionality by the addition of water, resulting in the cleavage of a chemical bond. Such enzymes are involved in key processes in the body. Enzymes according to this invention include lipases (hydrolyse fatty acid esters), esterases (hydrolyse esters) and phosphatases (hydrolyse phosphate esters).

The enzyme is preferably a lipase. Lipases include pancreatic lipase, gastric lipase, lipoprotein lipase, lingual lipase, adipose tissue lipase, hormone sensitive lipase, phospholipase A1, A2, B, C, D etc., hepatic lipase, and other triacyl, diacyl and monoacylglycerol lipases in the mammalian body. Many similar such lipases are also known in plants, fungi and microorganisms.

Also covered are esterase enzymes and phosphatase enzymes. Esterase enzymes include pig liver esterase, cholesteryl esterase, retinyl esterase, 1-alkyl-2-acetylglycerophosphocholine esterase, carboxylic ester hydrolases, and cholesterol esterase. Phosphatase enzymes include serine/threonine phosphatases PP1, PP2 and PP3, phosphoprotein phosphatase, myosin-light-chain phosphatase, protein phosphoprotein 2C, and protein tyrosine phosphatase.

The fifth aspect of the invention has important applications. It includes test and diagnostic methods and the control and inhibition of unwanted enzymes, preferably lipases, in any process or in any product. The processes or products, which preferably involve a lipase, include: processing of agricultural commodities (e.g. oilseeds), recovery and isolation of enzymes from biotechnological processes (e.g. involving lysis of microorganisms), the manufacture and extraction of crude oil (especially oil and plastics), the industrial manufacture of triglycerides or other fats, manufacture of healthcare goods which comprise surfactants, soap or detergent (e.g. bath oils, creams), the manufacturing and processing of liposomes (e.g. healthcare products, diagnostics, gene therapy), the treatment of industrial waste (e.g. paper effluent treatment) and preventing the degradation of foodstuff which comprises a fat (e.g. chocolate processing). Thus, the invention also relates to these products and processes, e.g. a foodstuff which comprises a compound according to the first aspect of the invention, in particular foodstuffs which have a high fat content such as cakes, biscuits, pastry-products and the like and chocolate products. The preferred features of the fifth aspect of the invention, including an enzyme whose preferred mode of action is to catalyse the hydrolysis of an ester functionality (in vivo, as the enzyme naturally occurs) are as discussed for the previous aspects of the invention.

All preferred features of the first, second, third and fourth aspects also apply to the fifth aspect of the present invention.

A sixth aspect of the invention provides a composition comprising a novel compound according to the first or second aspect of the invention, in combination with a pharmaceutically acceptable carrier or diluent. Suitable carriers and/or diluents are well known in the art and include pharmaceutical grade starch, mannitol, lactose, magnesium stearate, sodium saccharin, talcum, cellulose, glucose, sucrose, (or other sugar), magnesium carbonate, gelatin, oil, alcohol, detergents, emulsifiers or water (preferably sterile). The composition may be a mixed preparation of a composition or may be a combined preparation for simultaneous, separate or sequential use (including administration).

The compounds according to the invention for use in the aforementioned indications may be administered by any convenient method, for example by oral (including by inhalation), parenteral, mucosal (e.g. buccal, sublingual, nasal), rectal or transdermal administration and the compositions adapted accordingly.

For oral administration, the compounds can be formulated as liquids or solids, for example solutions, syrups, suspensions or emulsions, tablets, capsules and lozenges.

A liquid formulation will generally consist of a suspension or solution of the compound or physiologically acceptable salt in a suitable aqueous or non-aqueous liquid carrier(s) for example water, ethanol, glycerine, polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and microcrystalline cellulose.

A composition in the form of a capsule can be prepared using routine encapsulation procedures. For example, powders, granules or pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Compositions for oral administration may be designed to protect the active ingredient against degradation as it passes through the alimentary tract, for example by an outer coating of the formulation on a tablet or capsule.

Typical parenteral compositions consist of a solution or suspension of the compound or physiologically acceptable salt in a sterile aqueous or non-aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal or oral administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal or vaginal administration are conveniently in the form of suppositories (containing a conventional suppository base such as cocoa butter), pessaries, vaginal tabs, foams or enemas.

Compositions suitable for transdermal administration include ointments, gels, patches and injections including powder injections.

Conveniently the composition is in unit dose form such as a tablet, capsule or ampoule.

The compositions of the sixth aspect of the invention are useful in the prevention and/or treatment of obesity, obesity-related disorder, other medical weight loss and non-medical related weight loss. Preferred features of this aspect of the invention are as described above for the first to fifth aspects of the invention.

A seventh aspect of the invention provides a process for the manufacture of a composition according to the sixth aspect of the invention. The manufacture can be carried out by standard techniques well known in the art and involves combining a compound according to the second aspect of the invention and a pharmaceutically acceptable carrier or diluent. The composition may be in any form including a tablet, a liquid, a capsule, and a powder or in the form of a food product, e.g. a functional food. In the latter case the food product itself may act as the pharmaceutically acceptable carrier.

All preferred features of the first, second, third, fourth, fifth and sixth aspects also apply to the seventh aspect of the present invention.

An eighth aspect of the invention provides a method for the prevention or treatment of obesity or an obesity-related disorder, the method comprising the administration of a compound according to the first aspect or the second aspect of the invention, preferably in combination with a pharmaceutically acceptable carrier or diluent (as per the sixth aspect of the invention). Obesity-related disorders include hyperlipeamia, hyperlipideamia, hyperglycaemia, hypertension, cardiovascular disease, stroke, gastrointestinal disease and gastrointestinal conditions. The compound or composition is preferably administered to a patient in need thereof and in a quantity sufficient to prevent and/or treat the symptoms of the condition, disorder or disease. For all aspects of the invention, particularly medical ones, the administration of a compound or composition has a dosage regime which will ultimately be determined by the attending physician and will take into consideration such factors such as the compound being used, animal type, age, weight, severity of symptoms, method of administration, adverse reactions and/or other contraindications. Specific defined dosage ranges can be determined by standard design clinical trials with patient progress and recovery being fully monitored. Such trials may use an escalating dose design using a low percentage of the maximum tolerated dose in animals as the starting dose in man.

The physiologically acceptable compounds of the invention will normally be administered in a daily dosage regimen (for an adult patient) of, for example, an oral dose of between 1 mg and 2000 mg, preferably between 30 mg and 1000 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

All preferred features of the first, second, third, fourth, fifth, sixth and seventh aspects also apply to the eighth aspect of the present invention.

A ninth aspect of the invention provides a cosmetic method (non-therapeutic) for maintaining a given weight, or for cosmetic weight loss, the method comprising the administration of a compound according to the first or second aspect of the invention, preferably in combination with a pharmaceutically acceptable carrier or diluent (as per the sixth aspect of the invention). The compound or composition is preferably administered to a subject in need or in desideratum thereof and in a quantity sufficient to maintain a given weight or for cosmetic weight loss.

The eighth and ninth aspects of the invention relate to methods which are applicable to humans and other animals, in particular companion animals (such as dogs and cats) and other animals which provide meat for human consumption, such as cattle, pigs and sheep (all of any age).

All preferred features of the first, second, third, fourth, fifth, sixth, seventh and eighth aspects also apply to the ninth aspect of the present invention.

The invention will now be described with reference to the following non-limiting examples.

EXAMPLES

Synthesis of Novel Compounds According to the Invention

The foregoing description details specific compounds, compositions, methods and uses which can be employed to practice the present invention. However, those skilled in the art will know how to use alternative reliable methods for aiming at alternative embodiments of the invention which are herein encompassed.

Synthesis of 2-phenylamino-4H-thieno[2,3-d][1,3]oxazin-4-one

A solution of tert-butyl 2-aminothiophene-3-carboxylate (1) (0.1 g, 0.5 mmol) in pyridine (1 mL) was treated with phenyl isocyanate (65 microL, 0.6 mmol) and stirred at room temperature for 18 h. The mixture was then poured into 10% citric acid solution (10 mL) and the aqueous extracted with ethyl acetate (3×10 mL). The combined organic phase was dried (MgSO$_4$) and evaporated to give a cream solid. This was triturated with ethyl acetate and filtered to remove a white solid (25 mg) which was rinsed with ethyl acetate and discarded. The filtrate was then evaporated under reduced pressure and the resulting solid was triturated with cyclohexane to give the tert-butyl urea as a grey-white powder (0.13 g). M/z (ES$^+$) 319 (MH$^+$).

The crude tert-butyl urea (2) (50 mg, assume 0.19 mmol) was stirred in a solution of 20% CF$_3$CO$_2$H (TFA) in dichloromethane (10 mL) at room temperature for 3 h. The solvent was then evaporated to give a white powder which was used further without any purification. M/z (ES$^+$) 263 (MH$^+$)

The crude acid-urea (3) was suspended in dichloromethane (1 mL) and DMF (3-5 drops) added until dissolution was achieved. 1-(3-Dimethylamino-propyl)-3-ethylcarbodiimide hydrochloride (EDC, 44 mg, 0.23 mmol) was added and the reaction mixture stirred at room temperature for 12 h, poured into water and the aqueous extracted with dichloromethane (3×10 mL). The combined organic was washed with 2 portions of brine, dried (MgSO$_4$) and solvent evaporated to give a brown powder. This was dissolved in THF, adsorbed onto silica and purified by chromatography to afford the title compound (4) (85:15 petroleum ether:ethyl acetate plus a few drops of Et$_3$N). Yield: 15 mg, 32%; R$_f$ 0.34 (85:15 petroleum ether:EtOAc); $_H$(400 MHz, CDCl$_3$) 6.87 (1H, d, J5.8, Th-H), 7.00 (1H, s, NH), 7.11 (1H, t, J7.5, Ph-H), 7.23 (1H, d, J5.8, Th-H), 7.33 (2H, t, J7.9, Ph-H), 7.52 (2H, d, J8.1, Ph-H); m/z (ES$^+$) 244.9 (MH$^+$).

Reaction Scheme for the Preparation of 2-(4-Phenoxy)-phenylamino-4H-thieno[2,3-d][1,3]oxazin-4-one IV (compound 5)

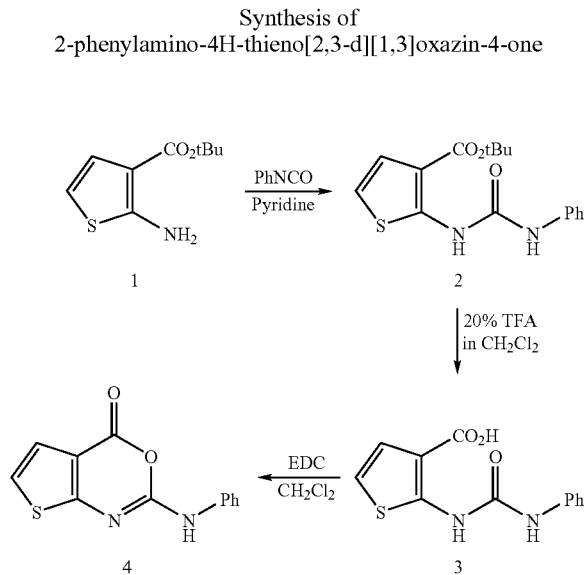

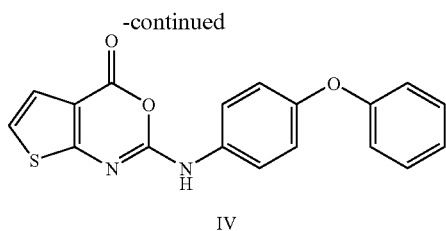

IV

2-Amino-thiophene-3-carboxylic acid tert-butyl ester I

A solution of 1,4 dithiane-2,5-diol (1.1 g) and t-butyl cyanoacetate (2.2 ml) in dry tetrahydrofuran (20 ml) was warmed to ~45° C. then treated slowly with triethylamine (2ml). The temperature rose to ~54° C. and a yellow colouration developed. The mixture was stirred at ~50° C. for a further 75 mins during which time the colour gradually darkened and became brownish. Water (200 ml) was added, then the mixture was acidified with acetic acid and extracted with ether. The ether extracts were washed with water, dried on magnesium sulfate, filtered and concentrated in vacuo. Residual acetic acid was removed by azeotropic distillation with toluene. The resulting brown liquid was identified as the desired product by NMR. The sample was used without further purification.

NMR(CDCl3) δ (ppm): 1.6 (9H, s); 5.85 (2H, br.s); 6.2 (1H, d); 6.95 (1H, d).

2-[3-(4-Phenoxy-phenyl)-ureido]-thiophene-3-carboxylic acid tert-butyl ester II To a solution of t-butyl 2-amino-thiophene-3-carboxylate (0.6 g) in dry pyridine (20 ml) was added 4-phenoxyphenyl-isocyanate (0.84 g). The mixture was stirred for 48 h, then the dark coloured solution was poured into water (200 ml). The stirred mixture was acidified with acetic acid and a precipitate slowly solidified to give a brown solid. After about 1 hr, the solid was filtered off, dried in vacuo and recrystallised from acetonitrile, giving an off-white solid. MP=203-205° C. Yield=0.6 g (48.8%).

2-[3-(4-Phenoxy-phenyl)-ureido]-thiophene-3-carboxylic acid III

The ester II (0.49 g) was dissolved in 40 ml dry dichloromethane, and 0.5 ml trifluoroacetic acid was added. After 16 hrs, tlc of a sample showed incomplete reaction. The solution was heated at reflux for 16 hrs by which time no ester remained by tlc. The solution was concentrated to dryness in vacuo and remaining solid was recrystallised from acetonitrile. MP=195-198° C. Yield=0.32 g (75.6%).

2-(4-Phenoxy-phenylamino)-4H-thieno[2,3-d][1,3]oxazin-4-one IV

To a solution of the acid III (266 mg) in dry dichloromethane (40 ml) and dry N,N-dimethylformamide (5 ml) was added 1-[3-(dimethylamino)propyl]-3-ethylcarbodiimide hydrochloride (0.2 g). The solution was stirred at room temperature overnight, then concentrated under reduced pressure. The residual liquid was diluted with water (150 ml). After being stirred for 1 hr, the white precipitate was extracted into ethyl acetate. The organic layers were separated, washed with water, dried on magnesium sulfate, filtered and concentrated in vacuo, giving an off-white solid. This was recrystallised from toluene to give a white solid. MP=206-210° C. Yield=129 mg (51.2%).

Reaction Scheme for the Preparation of 2-(4-Phenylsulfanyl)-phenylamino-4H-thieno[2,3d][1,3]oxazin-4-one VII (compound 16)

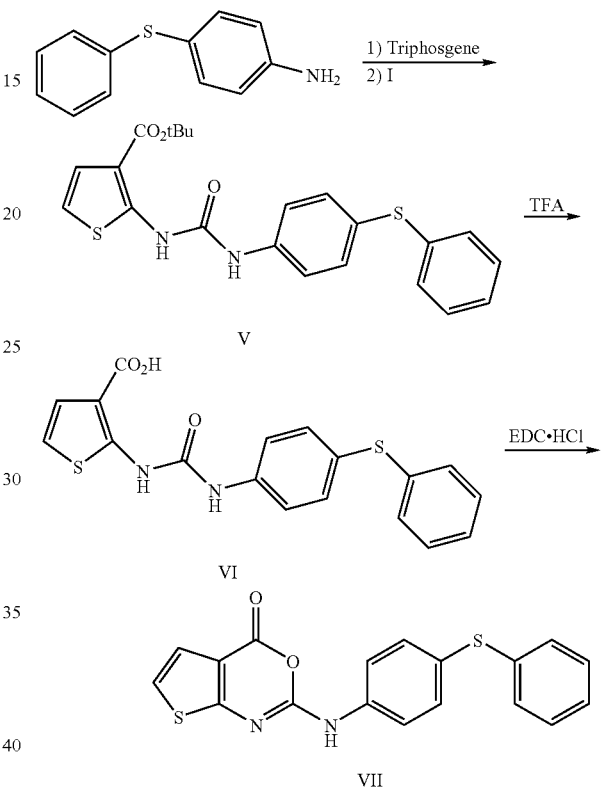

2-[3-(4-Phenylsulfanylphenyl)-ureido]thiophene-3-carboxytic acid tert-butyl ester V A solution of 4-phenylthioaniline (0.21 g) in dry dichloromethane (30 ml) was stirred at room temperature while triphosgene (0.1 g) was added followed by triethylamine (0.5 ml). The mixture was refluxed for 1 hr, then cooled to room temperature. The solvent was removed by rotary evaporation and the residue was dissolved in dry pyridine (30 ml). To this solution was added t-butyl 2-aminothiophene-3-carboxylate (0.2 g). This mixture was stirred at room temperature for 48 hrs. The solution was diluted with water and acidified with acetic acid. The ethyl acetate extracts were separated, dried on magnesium sulfate, filtered and evaporated to dryness under reduced pressure to give a viscous, brown oil. This oil was purified by flash column chromatography to give a white solid which was used without further purification. Yield=0.14 g (32.5%).

NMR(CDCl3) δ (ppm): 1.6 (9H, s); 6.6 (1H, d); 6.7 (1H, br.s); 7.1 (1H, d); 7.2 (1H, m); 7.3 (4H, m); 7.4 (4H, m); 10.7 (1H, br.s).

2-[3-(4-Phenylsulfanylphenylureido]thiophene-3-carboxylic acid VI

A solution of the ester V (125 mg) in dry dichloromethane (50 ml) was stirred at room temperature with trifluoroacetic acid (5 ml) overnight. The solution was concentrated to dryness in vacuo and the grey residue was recrystallised from acetonitrile. The product was obtained as a white solid. Yield=53 mg (48.6%).

NMR(CDCl$_3$, DMSO) δ (ppm): 6.6(1H, d); 7.2(5H, m); 7.4(4H, m); 7.55(2H, d); 9.85 (1H, br.s); 10.55(1H, br.s).

2-(4-Phenylsulfanylphenyl)-4H-thieno[2,3d][1,3]oxazin-4-one VII

To a solution of the acid VI (52 mg) in dry dichloromethane (20 ml) and dry N,N-dimethylformamide (2 ml) was added 1-[3-(dimethylamino)propyl]-3-ethylcarbodiimide hydrochloride (0.15 g). The mixture was stirred overnight. The volatiles were removed by rotary evaporation, then the residues were poured into water and stirred for 0.5 hrs before being extracted into ether. These organic layers were separated, washed well with water, dried on magnesium sulfate, filtered, and concentrated to dryness. The resulting pale yellow solid was recrystallised from toluene to give a very pale yellow solid. MP=203-204° C. Yield=24 mg (49.0%).

Reaction Scheme for the Preparation of 6-Methyl-2-(4-phenoxy)-4H-phenylamino-thieno[2,3-d][1,3]oxazin-4-one XI (compound 9)

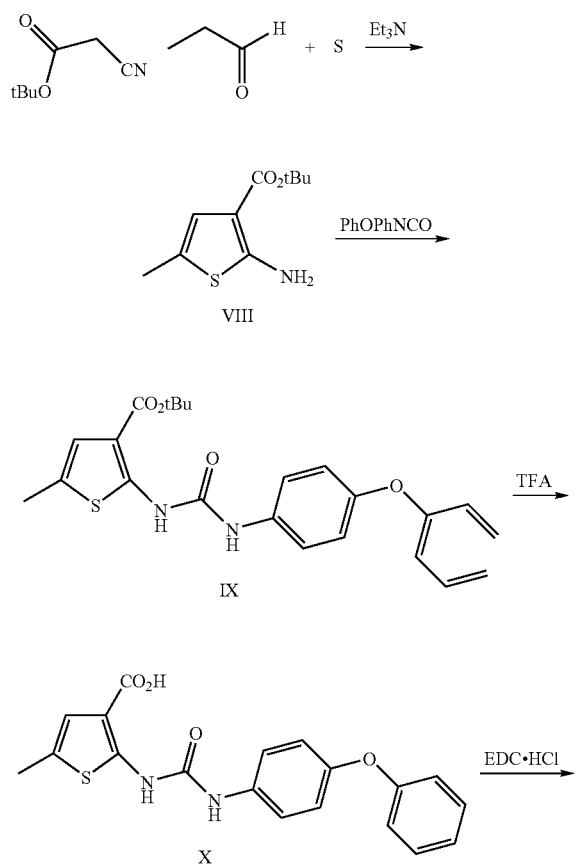

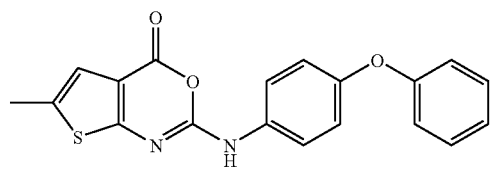

XI

2-Amino-5-methylthiophene-3-carboxylic acid tert-butyl ester VIII

To a suspension of methyl cyanoacetate (1.4 g) and sulfur (0.5 g) in dry N,N-dimethylformanide (3 ml) was added dry triethylamine (1.01 g). Propionaldehyde (1.24 g) was added dropwise to the reaction mixture, then the reaction mixture was heated at 70° C. for 1 hr. The mixture was poured into water and extracted with ether. The combined ether extracts were washed with brine, dried on magnesium sulfate, filtered and concentrated in vacuo. The crude was purified by flash chromatography on silica gel (Petroleum ether/ether 9/1) to give the title compound. Yield=1.54 g (72%).

NMR (CDCl$_3$): 1.5(9H, s); 2.25 (3H, s); 5.65 (2H, br.s); 6.55 (1H, s).

5-Methyl-2-[3-(4-phenoxyphenyl)ureido]-thiophene-3-carboxylic acid tert-butyl ester IX To a solution of t-butyl-5-methyl 2-amino-thiophene-3-carboxylate (0.5 g) in dry pyridine (5 ml) was added 4-phenoxyphenylisocyanate (0.31 g). The mixture was stirred overnight, then the solution was evaporated. The solid was triturated in diisopropyl ether and the precipitate filtered off. MP=130-132° C. Yield=0.68 g (71%).

5-Methyl-2-[3-(4-phenoxyphenyl)ureido]thiophene-3-carboxylic acid X

A solution of the ester IX (0.42 g) in dry dichloromethane (50 ml) was refluxed two hours with trifluoroacetic acid (4 ml). When tlc indicated no remaining starter, the solution was concentrated to dryness in vacuo to give a solid residue. Yield=0.4 g (100%) MP=213-215° C.

6-Methyl-2-(4-phenoxyphenylamino)-4H-thieno[2,3-d][1,3]oxazin-4-one XI

To a solution of the acid X (150 mg) in dry dichloromethane (10 ml) and dry N,N-dimethylformamide (15 ml) was added 1-[3-(dimethylamino)propyl]-3-ethylcarbodiimide hydrochloride (82 mg). The solution was stirred at room temperature overnight, then concentrated under reduced pressure. Water was added to the residual liquid and the white precipitate formed, filtered off. This was recrystallised from toluene to give a white solid. Yield=26 mg(18%).

NMR (DMSO): 2.65 (3H, s); 7.15 (3H, m); 7.32 (3H, m); 7.6 (2H, t); 7.8 (2H, t); 10.85 (1H, s).

Biological Test Methods and Results

Test Compounds

The thieno-oxazinone compounds used in the following tests are identified by the reference number assigned in Table 1 hereinbefore.

Measurement of Lipase Activity Using a Quinine Diimine Dye Calorimetric Assay

The inhibitory activity of the selected compounds to pancreatic lipase was measured in the following assay available from Sigma Ltd (Lipase-PS™, catalog number 805-A):

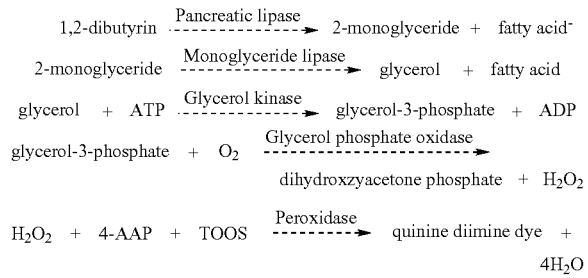

The glycerol released from the action of pancreatic and monoglyceride lipase was oxidised to release $H_2O_2$. The peroxidase reaction step then produces a quinine dye which is pink in colour and absorbs light at a wavelength of 550 nm.

Inhibitor

Individual test compounds were dissolved in DMSO (dimethyl sulphoxide) at 10 mM. DMSO was used to avoid any problems with compounds being water-insoluble.

For individual compounds, the $IC_{50}$ (concentration at which lipase activity is inhibited to one half of the maximum) was calculated by measuring the inhibitory activity from log-dose response curves using a range of inhibitor concentrations.

Measurement of Lipase Enzyme Activity Using a NaOH Titration Method

The inhibitory activity of the selected compound to pancreatic lipase was measured in the assay described in Pasquier et al; 1996, Vol 7, *Nutritional Biochemistry*, 293-302.

Log dose/response curves were constructed using a range of inhibitor concentrations.

Measurement of Cholesterol Esterase Activity

Bovine pancreatic cholesterol esterase (Sigma Cat. No. C5921) was dissolved at 1 mg/ml in 100 mM MOPS 2 mM $CaCl_2$ pH 7.3. Selected compounds were routinely stored as 5 mM stock solutions dissolved in DMSO (Dimethylsulphoxide) at −20° C. Prior to use, the stock was further diluted in 40% DMSO (60% 100 mM MOPS 2 mM CaCl2 pH 7.3) to give a series of dilutions (×20, ×100, ×200, ×1,000, ×2,000, ×10,000, ×20,000 and ×100,000)

The assay substrate contained p-Nitrophenyl butyrate (Sigma Cat. No. N9876) MW 209.2. Density 1.2 and Taurocholic acid, sodium salt (Sigma Cat. No. T 4009) MW 537.7 The assay substrate was prepared by dissolving 43 mg Taurocholic acid (6 mM final concentration)+87 μl p-Nitrophenyl butyrate (40 μM final concentration)+50 μl 20% Triton X-100 (0.08% final concentration) in 10 ml of 100 mM MOPS 2 mM $CaCl_2$ pH 7.3. The substrate was shaken to dissolve the ingredients and centrifuged to clarify.

The assay was prepared by mixing 10 μl enzyme, 50 μl inhibitor and 190 μl substrate in a 96 well ELISA plate in triplicate. The plates were incubated at 37° C. in a BioRad Benchmark Microplate reader and the rate of colour development over a 10 minute period was measured relative to that of the enzyme without inhibitor.

Measurement of Trypsin Activity

Porcine trypsin (Boehringer) was dissolved at a concentration of 1 mg/ml in 100 mM MOPS (3-[-Morpholino]propanesulphonic acid) pH 7.3 containing 2 mM $CaCl_2$. Prior to use, the enzyme was diluted 500 times to give a final concentration of 2 μg/ml.

Selected compounds were routinely stored as 5 mM stock solutions dissolved in DMSO (Dimethylsulphoxide) at −20° C. For the assay, aliquots were defrosted and a series of dilutions (×100, ×200, ×1,000, ×2,000, ×10,000, ×20,000 and ×100,000) made in 100 mM MOPS pH 7.3 containing 2 mM $CaCl_2$. The substrate Bz-Phe-Val-Arg-pNA (Benzoyl-phenylalanyl-valyl-arginine-p-nitroanilide) was dissolved in DMSO to give a 10 mM solution. Immediately prior to use, the substrate was diluted to 0.3 mM (30 μl/ml) in 100 mM MOPS containing 2 M $CaCl_2$.

The assay was set up in triplicate in a 96 well ELISA plate. 10 μl 2 μg/ml trypsin, 26 μl diluted inhibitor and 190 μl substrate were added sequentially. The plates were then incubated at 37° C. in a BioRad Benchmark Microplate Reader. The rate of release of p-nitroaniline was measured at 405 nM over 10 minutes relative to that of the enzyme without inhibitor.

Results

A range of standard compounds were assayed in the quinine dye calorimetric assay which provides a rapid method to measure lipase inhibitory activity. None of the compounds tested interfered with the colorimetric reaction i.e. they did not give false positive results.

A range of inhibitory activities for the tested compound was observed, indicating that these compounds are inhibitors of human pancreatic lipase. Compounds 1, 5, 6, 7, 8, 9, 10, 11, 12, 14, 15, 16, 18, 19, 20, 21, 23, 24, 25, 26, 27, 28, 29, 30, 31, 32, 33, 34, 35, 38, 40, 41, 43, 44, 45, 46, 47, 48, 49 and 50 exhibited an IC50<100 nM.

Selected thieno-oxazinone compounds were tested in the NaOH titration assay. In this assay, the activity of porcine pancreatic lipase in a system containing lipid micelles is recorded. These conditions are therefore similar to those encountered in the gastrointestinal tract.

A range of inhibitory activities were observed for the tested thieno-oxazinone 5 compounds in this assay, indicating that these compounds are inhibitors of porcine pancreatic lipase. Compounds 1, 5, 6, 7, 8, 9, 10, 11, 12, 14, 15, 16, 43, 44, 45, 46, 47, 48, 49 and 50 had an IC50 value of less than or equal to 1 microMolar.

The results demonstrate that a number of selected thieno-oxazinones are inhibitors of fat digestion and that these compounds may be particularly suitable for the treatment of obesity.

The activity of a number of selected thieno-oxazinone-compounds against trypsin and cholesterol esterase was measured in the assays described above. These compounds had no inhibitory activity towards trypsin or cholesterol esterase. Thus, the selected thieno-oxazinone compounds are highly selective lipase inhibitors.

While the preferred embodiment of the invention has been illustrated and described, it will be appreciated that various changes can be made therein without departing from the spirit and scope of the invention.

The invention claimed is:

1. A compound of formula (Ia)

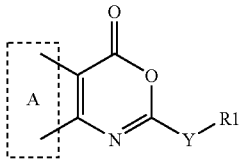

or a pharmaceutically acceptable salt or ester thereof;
wherein A is a thiophenyl moiety that is optionally substituted with one or more of alkyl, aryl, halo, alkoxy, haloalkyl, aryloxy, amino, heteroaryl, or arylalkyl;
Y is O, S or NR$^2$, wherein R$^2$ is hydrogen or an alkyl group having 1 to 6 carbon atoms;
and R$^1$ is
an unbranched alkyl group having from 6 to 25 carbon atoms, a branched alkyl group having from 6 to 25 carbon atoms, an arylalkyl group wherein the alkyl moiety has from 4 to 12 carbon atoms;
or
a phenyl group substituted with one or more optionally substituted phenyloxy, phenylthio, SO-phenyl, SO$_2$-phenyl, alkylphenyl, CO-phenyl, CO$_2$-phenyl, CONR$^{16}$-phenyl, NR$^{16}$CO-phenyl or NR$^{16}$-phenyl groups, wherein R$^{16}$ is hydrogen or an alkyl group having from 1 to 4 carbon atoms, and wherein the phenyloxy, phenylthio, SO-phenyl, SO$_2$-phenyl, alkylphenyl, CO-phenyl, CO$_2$-phenyl, CONR$^{16}$-phenyl, NR$^{16}$CO-phenyl or NR$^{16}$-phenyl groups are optionally substituted with one or more of halo, cyano, nitro, alkyl, alkylhalo, alkoxy, aryl, alkylaryl, aryloxy, amino, hydroxy or heteroaryl;
or
a phenyl group substituted with one or more of halo, NR$^6$R$^7$, OR$^6$, SR$^6$, COR$^6$, CO$_2$R$^6$, nitro, cyano, aryl, hetereoaryl, alkyl aryl, alkyl, haloalkyl or alkoxy with the proviso that said compound is not 5-methyl-2-(4-methoxyphenyl)amino-4H-thieno[2,3-d][1,3]oxazin-4-one, 6-pentyl-2-(4-chlorophenyl)amino-4H-thieno[2,3-d][1,3]oxazin-4-one or 6-pentyl-2-(4-methoxyphenyl) amino-4H-thieno[2,3-d][1,3]oxazin-4-one.

2. The compound of claim 1 wherein the compound is of formula IIa

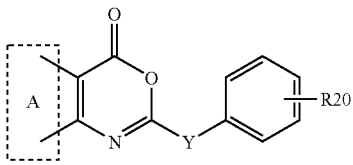

and pharmaceutically acceptable salts or esters thereof;
wherein group A is as defined in claim 1 for formula (Ia);
Y is as defined in claim 1 for formula (Ia);
and R$^{20}$ is phenyloxy, phenylthio, SO-phenyl, SO$_2$-phenyl, alkylphenyl, CO-phenyl, CO$_2$-phenyl, CONR$^6$-phenyl, NR$^6$CO-phenyl or NR$^6$-phenyl, optionally substituted with one or more of halo, cyano, alkyl, alkylhalo, alkoxy, aryl, alkylaryl, aryloxy, amino, hydroxy or heteroaryl.

3. The compound of claim 1 selected from the group consisting of:
2-Phenylamino-4H-thieno[2,3-d][1,3]oxazin-4-one
2-Butyloxy-4H-thieno-[2,3-d][1,3]oxazin-4-one
5-Methyl-2-phenylamino-4H-thieno[2,3-d][1,3]oxazin-4-one
5,6-Dimethyl-2-phenylamino-4H-thieno[2,3-d][1,3]oxazin-4-one
2-(4-Phenoxy)phenylamino-4H-thieno[2,3-d][1,3]oxazin-4-one
5-Phenyl-2-phenylamino-4H-thieno[3,2-d][1,3]oxazin-4-one
2-(4-(3-Trifluoromethyl-phenoxy)phenylamino)-4H-thieno[2,3-d][1,3]oxazin-4-one
5-(1,1-Dimethylethyl)-2-phenylamino-4H-thieno[3,2-d][1,3]oxazin-4-one
6-Methyl-2-(4-phenoxy)phenylamino-4H-thieno[2,3-d][1,3]oxazin-4-one
2-(4-Phenoxy)phenylamino-4H-thieno[3,2-d][1,3]oxazin-4-one
2-(4-Phenylmethyl)phenylamino-4H-thieno[2,3-d][1,3]oxazin-4-one
2-(4-Benzoyl)phenylamino-4H-thieno[2,3-d][1,3]oxazin-4-one
6-Methyl-2-(4-phenoxy)phenoxy-4H-thieno[2,3-d][1,3]oxazin-4-one
2-(4-(4-Trifluoromethyl-phenoxy)phenylamino)-4H-thieno[2,3-d][1,3]oxazin-4-one
2-(4-(3-Trifluoromethyl-phenoxy)phenoxy)-4H-thieno[3,2-d][1,3]oxazin-4-one
2-(4-Phenylthio) phenylamino-4H-thieno[2,3-d][1,3]oxazin-4-one
5,6-Dimethyl-2-(4-phenoxy)phenoxy-4H-thieno [2,3-d][1,3]oxazin-4-one
2-Dodecylamino-6-methyl-4H-thieno[2,3-d][1,3]oxazin-4-one
2-N-Dodecyl-N-methylamino-6-methyl-4H-thieno[2,3-d][1,3]oxazin-4-one
2-Dodecylamino-4H-thieno[2,3-d][1,3]oxazin-4-one
2-Dodecylthio-6-methyl-4H-thieno[2,3-d][1,3]oxazin-4-one
2-(4-N-(1-Methylethyl)-N-phenylamino)phenylamino-4H-thieno[2,3-d][1,3]oxazin-4-one
2-(4-Phenylsulfonyl) phenylamino-4H-thieno[2,3-d][1,3]oxazin-4-one
2-(4-Phenylcarbamoyl) phenylamino-4H-thieno[2,3-d][1,3]oxazin-4-one
2-(4-(4-Chlorophenoxy)-phenylamino)-4H-thieno[2,3-d][1,3]oxazin-4-one
2-(4-(4-Methylphenoxy)-phenylamino)-4H-thieno[2,3-d][1,3]oxazin-4-one
2-(4-Cyanophenyl)amino-4H-thieno[2,3-d][1,3]oxazin-4-one
2-(4-Cyanophenyl)amino-6-propyl-4H-thieno[2,3-d][1,3]oxazin-4-one
2-(4-Cyanophenyl)amino-6-methyl-4H-thieno[2,3-d][1,3]oxazin-4-one
6-Phenylmethyl-2-(4-cyanophenyl)amino-4H-thieno[2,3-d][1,3]oxazin-4-one
2-(4-Cyanophenyl)amino-6-dodecyl-4H-thieno [2,3-d][1,3] oxazin-4-one
6-Methyl-2-(4-phenylbutyl) amino-4H-thieno [2,3-d][1,3]oxazin-4-one
2-(2-Chloroethyl)amino-6-methyl-4H-thieno [2,3-d][1,3] oxazin-4-one
2-(Hept-6-enyl)amino-6-methyl-4H-thieno[2,3-d][1,3] oxazin-4-one 2-(5-Methoxycarbonylpentyl) amino-6-methyl-4H-thieno [2,3-d][1,3]oxazin-4-one
2-Phenylamino-5,6,7,8-tetrahydro-4H-benzothieno[2,3-d][1,3]oxazin-4-one
2-(4-Phenoxy)phenylamino-4H-thieno-[3,4-d][1,3]oxazin-4-one
2-(4-(4-Trifluoromethylphenoxy)phenylamino)-4H-thieno[3,2-d][1,3]oxazin-4-one
2-(4-Cyanophenyl)amino-4H-thieno[3,2-d][1,3]oxazin-4-one
2-Dodecylamino-4H-thieno[3,2-d][1,3]oxazin-4-one
2-(5-Methylhexyl)amino-4H-thieno[3,2-d][1,3]oxazin-4-one
5-Methyl-2-(4-phenoxy)phenylamino-4H-thieno[3,2-d][1,3]oxazin-4-one
6-Propyl-2-(4-phenoxy)phenylamino-4H-thieno[2,3-d][1,3]oxazin-4-one
2-Hexadecylamino-6-methyl-4H-thieno-[2,3-d][1,3]oxazin-4-one
6-Chloro-2-(4-phenoxy)phenylamino-4H-thieno [2,3-d][1,3]oxazin-4-one
6-Dodecyl-2-(4-phenoxy)phenylamino-4H-thieno [2,3-d][1,3]oxazin-4-one
6-Phenylmethyl-2-(4-phenoxy)phenylamino-4H-thieno [2,3-d][1,3]oxazin-4-one
6-(4-Phenoxyphenylamino)-7-oxa-9-thia-1,5-diazafluoren-8-one
2(5,5,5-Trifluoropentyl)amino-4H-thieno [2,3-d][1,3]oxazin-4-one
2-Eicosylamino-4H-thieno[2,3-d][1,3]oxazin-4-one
2-Octadecylamino-4H-thieno [2,3-d][1,3]oxazin-4-one
2-Hexadecyloxy-4H-thieno [2,3-d][1,3]oxazin-4-one
2-(12-Nitrododecyl)-amino-4H-thieno [2,3-d][1,3]oxazin-4-one
2-(12-Phenyldodecyl)-amino-4H-thieno [2,3-d][1,3]oxazin-4-one
2-(12-(Pyrid-2-yl)dodecyl)-amino-4H-thieno [2,3-d][1,3]oxazin-4-one
2-Octylamino-4H-thieno [2,3-d][1,3]oxazin-4-one
2-(8-Phenyloctyl)amino-4H-thieno [2,3-d][1,3]oxazin-4-one
2-(4-Phenylsulfinyl)-phenylamino-4H-thieno [2,3-d][1,3]oxazin-4-one
2-(4-Phenoxycarbonyl)-phenylamino-4H-thieno [2,3-d][1,3]oxazin-4-one
2(4-(4-Methoxyphenoxy)-phenylamino)-4H-thieno[2,3-d][1,3]oxazin-4-one
2(4-(4-Dimethylaminophenoxy)-phenylamino)-4H-thieno[2,3-d][1,3]oxazin-4-one
2(4-(4-Hydroxyphenoxy)-phenylamino)-4H-thieno[2,3-d][1,3]oxazin-4-one
2(3-Phenoxy)-phenylamino-4H-thieno[2,3-d][1,3]oxazin-4-one
2(2-Phenoxy)-phenylamino-4H-thieno[2,3-d][1,3]oxazin-4-one
2-(3-Cyanophenyl)amino-6-methyl-4H-thieno[2,3-d][1,3]oxazin-4-one
2-(4-Chlorophenyl)amino-6-methyl-4H-thieno[2,3-d][1,3]oxazin-4-one
2-(4-Aminophenyl)amino-4H-thieno[2,3-d][1,3]oxazin-4-one
2-(4-Hydroxyphenyl)amino-4H-thieno[2,3-d][1,3]oxazin-4-one
2-(4-Methoxycarbonylphenyl)amino-4H-thieno[2,3-d][1,3]oxazin-4-one
2-(4-Trifluoromethylphenyl)amino-4H-thieno[2,3-d][1,3]oxazin-4-one
2-N-(4-Phenoxy)phenyl-N-ethylamino-4H-thieno[2,3-d][1,3]oxazin-4-one
2-N-(4-Phenoxy)phenyl-N-1-methylethylamino-4H-thieno[2,3-d][1,3]oxazin-4-one
6-Cyclopropyl-2-(4-phenoxy)-phenylamino-4H-thieno[2,3-d][1,3]oxazin-4-one
2-(4-Phenoxy)phenyl-thio-4H-thieno[2,3-d][1,3]oxazin-4-one
2-(4-Phenoxy)phenylamino-6-trifluoromethyl-4H-thieno[2,3-d][1,3]oxazin-4-one
6-Methoxy-2-(4-phenoxy)phenylamino-4H-thieno[2,3-d][1,3]oxazin-4-one
6-Phenoxy-2-(4-phenoxy)phenylamino-4H-thieno[2,3-d][1,3]oxazin-4-one
6-Methyl-2-(4-methoxyphenyl)amino-4H-thieno[2,3-d][1,3]oxazin-4-one
2-(4-Phenoxy)phenylamino-6-propyl-4H-thieno[2,3-d][1,3]oxazin-4-one
6-Cyano-2-(4-phenoxy)phenylamino-4H-thieno[2,3-d][1,3]oxazin-4-one
6-Chloro-2-(4-phenoxy)phenylamino-4H-thieno[2,3-d][1,3]oxazin-4-one
6-Methyl-2-(4-phenoxy)phenylthio-4H-thieno[2,3-d][1,3]oxazin-4-one
6-Methyl-2-(4-phenoxy)phenoxy-4H-thieno[2,3-d][1,3]oxazin-4-one
6-Methyl-2-(4-phenoxy)phenoxy-4H-thieno[3,2-d][1,3]oxazin-4-one
7-Methyl-2-(4-phenoxy)phenylamino-4H-thieno[3,4-d][1,3]oxazin-4-one
5-Methyl-2-(4-phenoxy)phenylamino-4H-thieno[3,4-d][1,3]oxazin-4-one
6-Methyl-2-(4-phenoxy)phenylamino-4H-thieno[2,3-d][1,3]oxazin-4-one
6-Methyl-2-(3-methylisoxazol-5-yl)amino-4H-thieno[2,3-d][1,3]oxazin-4-one.

4. The compound of claim 1 which is 6-methyl-2-(4-phenoxy)phenylamino-4H-thieno[2,3-d][1,3]oxazin-4-one.

5. A process for the preparation of a compound of formula (Ia) as defined in claim 1 which process comprises:

Process (A): reacting a compound of formula (IV):

(IV)

with a compound of formula (V):

(V)

wherein groups A, Y and R$^1$ are as defined in claim 1;

or:

Process (B): cyclising a compound of formula (VI):

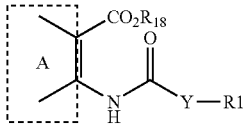

(VI)

wherein groups A, Y and $R^1$ are as defined in claim 1 and $R^{18}$ is hydrogen or $C_{1-6}$alkyl;

or:

Process (C): reacting a compound of formula (VII):

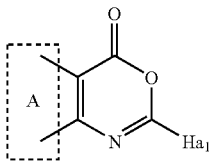

(VII)

with a compound of formula (VIII):

 (VIII)

wherein groups A, Y and $R^1$ are as defined in claim 1 and $Ha_1$ is a halide;

or:

Process (D): reacting a compound of formula (IX):

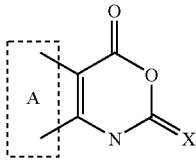

(IX)

wherein group A is as defined in claim 1 and X is O, S or NH, with a compound of formula (X):

 (X)

wherein group $R^1$ is as defined in claim 1;

or:

Process (E) converting a compound of formula (Ia) into a different compound of formula (Ia) by:

(i) reduction of a compound of formula (Ia) wherein $R^1$ or $R^2$ or any substituent on the heterocyclic group A contains an alkenyl or alkynyl group or moiety, to the corresponding alkyl or alkenyl group or moiety; or (ii) alkylation of a compound of formula (Ia) where one or more substituent on the heterocyclic group A represents a halogen atom.

6. A method for the treatment of obesity, the method comprising administering to a patient a compound of any one of claims 1 to 4.

7. The method for the treatment of an obesity-related disorder selected from one or more of hyperlipaemia, hyperlipidaemia, hyperglycaemia (type II diabetes), or hypertension, the method comprising administering to a patient a compound of any one of claims 1 to 4.

8. The method of claim 6 wherein the compound inhibits a lipase enzyme involved in the metabolism or degradation of a fat.

9. A method for reducing levels of dioxins and polychlorinated biphenyls (PCBs) in body fat, the method comprising administering to a patient a compound as defined in any one of claims 1 to 4.

10. The method of claim 6 wherein the patient is a human.

11. The method of claim 6 wherein the patient is an animal.

12. The method of claim 6 wherein the compound inhibits a lipase enzyme.

13. A pharmaceutical composition comprising the compound of any one of claims 1 to 4 in combination with a pharmaceutically acceptable carrier or diluent.

14. A method for the treatment of obesity or an obesity-related disorder selected from one or more of hyperlipaemia, hyperlipidaemia, hyperglycaemia (type II diabetes), or hypertension, the method comprising administering to a patient, a compound of any one of claims 1 to 4, a pharmaceutical composition comprising the compound of any one of claims 1 to 4 in combination with a pharmaceutically acceptable carrier or diluent, or a food product comprising the compound of any one of claims 1 to 4.

15. A method for inhibiting an enzyme in vitro, comprising contacting the enzyme with a compound of formula (Ia) or (IIa) as defined in claim 1 or 2, wherein the enzyme is a lipase.

16. A method for reducing fat content of animals, the method comprising administering to an animal a compound of formula (Ia) or (IIa) as defined in claim 1 or 2.

17. A method for maintaining a given weight, or for weight loss, the method comprising administering to a patient a compound of formula (Ia) or (IIa) as defined in claim 1 or 2.

18. A process for the preparation of a compound of formula (IIa) as defined in claim 2 which process comprises:

Process (A): reacting a compound of formula (IV):

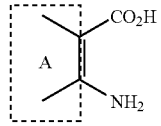

(IV)

with a compound of formula (V):

(V)

wherein groups A, Y and $R^1$ are as defined in claim 2;

or:

Process (B): cyclising a compound of formula (VI):

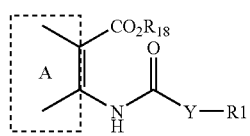

(VI)

wherein groups A, Y and $R^1$ are as defined in claim 2 and $R^{18}$ is hydrogen or $C_{1-6}$alkyl;

or:

Process (C): reacting a compound of formula (VII):

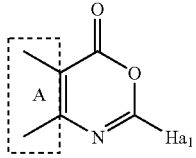

(VII)

with a compound of formula (VIII):

 (VIII)

wherein groups A, Y and $R^1$ are as defined in claim 2 and $Ha_1$ is a halide;

or:

Process (D): reacting a compound of formula (IX):

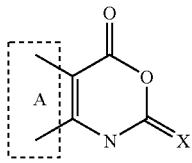

(IX)

wherein group A is as defined in claim 2 and X is O, S or NH, with a compound of formula (X):

 (X)

wherein group $R^1$ is as defined in claim 2;

or:

Process (E) converting a compound of formula (IIa) into a different compound of formula (IIa) by:

(i) reduction of a compound of formula (IIa) wherein $R^1$ or $R^2$ or any substituent on the heterocyclic group A contains an alkenyl or alkynyl group or moiety, to the corresponding alkyl or alkenyl group or moiety; or (ii) alkylation of a compound of formula (IIa) where one or more substituent on the heterocyclic group A represents a halogen atom.

19. The pharmaceutical composition of claim 13 wherein the compound is present in an amount sufficient to inhibit a lipase enzyme.

20. The pharmaceutical composition of claim 13 wherein the compound is present in an amount sufficient to treat a condition selected from obesity or an obesity-related disorder selected from one or more of hyperlipaemia, hyperlipidaemia, hyperglycaemia (type II diabetes), or hypertension.

21. The pharmaceutical composition of claim 13 wherein the compound is present in an amount sufficient to reduce levels of toxins in body fat.

22. The pharmaceutical composition of claim 13 wherein the composition is formulated for administration to humans.

23. The pharmaceutical composition of claim 13 wherein the composition is formulated for administration to animals.

24. A process for preparing a pharmaceutical composition comprising providing a compound of any one of claims 1 to 4; and mixing the compound with a pharmaceutically acceptable carrier or diluent.

25. The method of claim 9 wherein the patient is a human.

26. The method of claim 9 wherein the patient is an animal.

27. The method of claim 9 wherein the compound inhibits a lipase enzyme.

28. A pharmaceutically acceptable salt of a compound of claim 3.

29. A pharmaceutically acceptable ester of a compound of claim 3.

* * * * *